United States Patent [19]

Dupont et al.

[11] Patent Number: 6,025,334

[45] Date of Patent: *Feb. 15, 2000

[54] EXTRACTS OF SHARK CARTILAGE HAVING ANTI-COLLAGENOLYTIC, ANTI-INFLAMMATORY, ANTI-ANGIOGENIC AND ANTI-TUMORAL ACTIVITIES; PROCESS OF MAKING, METHODS OF USING AND COMPOSITIONS THEREOF

[75] Inventors: Eric Dupont, St. Nicolas; Paul Brazeau, Montreal; Christina Juneau, Ste. Foy, all of Canada; Daniel H. Maes, Huntington; Kenneth Marenus, Dix Hills, both of N.Y.

[73] Assignee: Les Laboratoires Aeterna Inc., Canada

[*] Notice: This patent is subject to a terminal disclaimer.

[21] Appl. No.: 08/550,003

[22] Filed: Oct. 30, 1995

Related U.S. Application Data

[63] Continuation-in-part of application No. 08/384,555, Feb. 3, 1995, Pat. No. 5,618,925, which is a continuation-in-part of application No. 08/234,019, Apr. 28, 1994, abandoned.

[51] Int. Cl.$^7$ .............................. A61K 38/00; C07K 1/00; A21J 1/00

[52] U.S. Cl. ............................ 514/21; 514/828; 514/855; 514/859; 514/863; 514/886; 514/887; 530/400; 530/412; 530/414; 530/415; 530/417; 530/418; 530/427

[58] Field of Search .............................. 514/21, 828, 855, 514/859, 863, 886, 887; 530/400, 412, 414, 415, 417, 418, 427

[56] References Cited

U.S. PATENT DOCUMENTS

| | | | |
|---|---|---|---|
| 3,478,146 | 11/1969 | Balassa | 424/95 |
| 4,042,457 | 8/1977 | Kuettner et al. | 530/356 |
| 4,243,582 | 1/1981 | Spilburg et al. | 530/395 |
| 4,350,682 | 9/1982 | Balassa | 424/64 |
| 4,356,261 | 10/1982 | Kuettner | 435/68 |
| 4,473,551 | 9/1984 | Schinitsky | 424/95 |
| 4,656,137 | 4/1987 | Balassa | 435/267 |
| 4,746,729 | 5/1988 | Kuettner et al. | 530/353 |
| 4,749,522 | 6/1988 | Kamarei | 424/95 |
| 4,822,607 | 4/1989 | Balassa et al. | 424/95 |
| 5,075,112 | 12/1991 | Lane | 424/434 |

FOREIGN PATENT DOCUMENTS

| | | |
|---|---|---|
| WO 94/12510 | 6/1994 | WIPO . |
| WO 95/03036 | 2/1995 | WIPO . |
| WO95/32722 | 12/1995 | WIPO . |

OTHER PUBLICATIONS

Lee et al, Science, vol. 221, 1185–1187, 1983.

Chabot–Fletcher, M. et al. (1994). "Interleukin–8 Production is Regulated by Protein Kinase C in Human Keratinocytes". *The Journal of Investigative Dermatology* 103(4): 509–515, 1994.

Folkman, J. and M. Klagsbrun (1987). "Angiogenic Factors". *Science*. 235: 442–446.

Langer, R et al. (1976). "Isolation of a Cartilage Factor That Inhibits Tumor Neovascularisation". *Science*. 193: 70–72.

Lee, A. and R. Langer (1983). "Shark Cartilage Contains Inhibitors of Tumor Angiogenesis". *Science*. 221: 1185–1187.

Luer, C.A. (1986). "Inhibitors of Angiogenesis from Shark Cartilage". *Fed. Proc.* 45(4): 949, Abstract 4624.

Moses, M.A. and R. Langer (1991). "Inhibitors of Angiogenesis". *Biotechnology* 9:630–634.

Nickoloff, B.J. et al. (1994). "Aberrant Production of Interleukin–8 and Thrombospondin–1 Psoriastic Keratinocytes Mediates Angiogenesis". *Am. J.Pathology* 144(4): 820–828.

Oikawa, T. et al. (1990) "A novel angiogenic inhibitor derived from Japanese shark cartilage (I). Extraction and estimation of inhibitory activities toward tumor and embyronic angiogenesis". *Cancer Letters* 51: 181–186.

Suzuki, F. et al. (1984). "Cartilage–derived Antitumor Factor (CATF): A High Molecular Weight Fraction in Cartilage Extract Inhibits Solid Tumor Growth". *J. of Bone and Mineral Metabolism* 2 (3): 3–7.

*Primary Examiner*—Cecilia J. Tsang
*Assistant Examiner*—Abdel A. Mohamed
*Attorney, Agent, or Firm*—Rick Matos; Akin, Gump, Strauss, Hauer & Feld, L.L.P.

[57] ABSTRACT

The present invention relates to cartilage extracts and to a method of producing the same. Shark cartilage extracts having anti-angiogenic, direct anti-tumor proliferating, anti-inflammatory and anti-collagenolytic activities have been obtained by an improved process. The process comprises the steps of obtaining a homogenate of cartilage in an aqueous solution, this homogenate being centrifuged and further fractionated to obtain a total extract having molecules of a molecular weight comprised between 0 to 500 KDa. The composition of the liquid extract has then been investigated by different ways. Further fractionation of this extract led to the preliminary characterization of some of its active components. Due to the multiplicity of biological activities of the total liquid extract, it can be used for treating numerous diseases or conditions such as those having components selected from the group consisting of tumor proliferation, angiogenesis, inflammation and collagenolysis. This extract has no offensive effect on normal body functions. Therefore, this shark cartilage extract has a very promising therapeutic value. The process for the obtention of cartilage extracts is simple and efficient. The unexpectedly valuable products obtained by this process are therefore an indication of a new and non-obvious process.

28 Claims, 17 Drawing Sheets

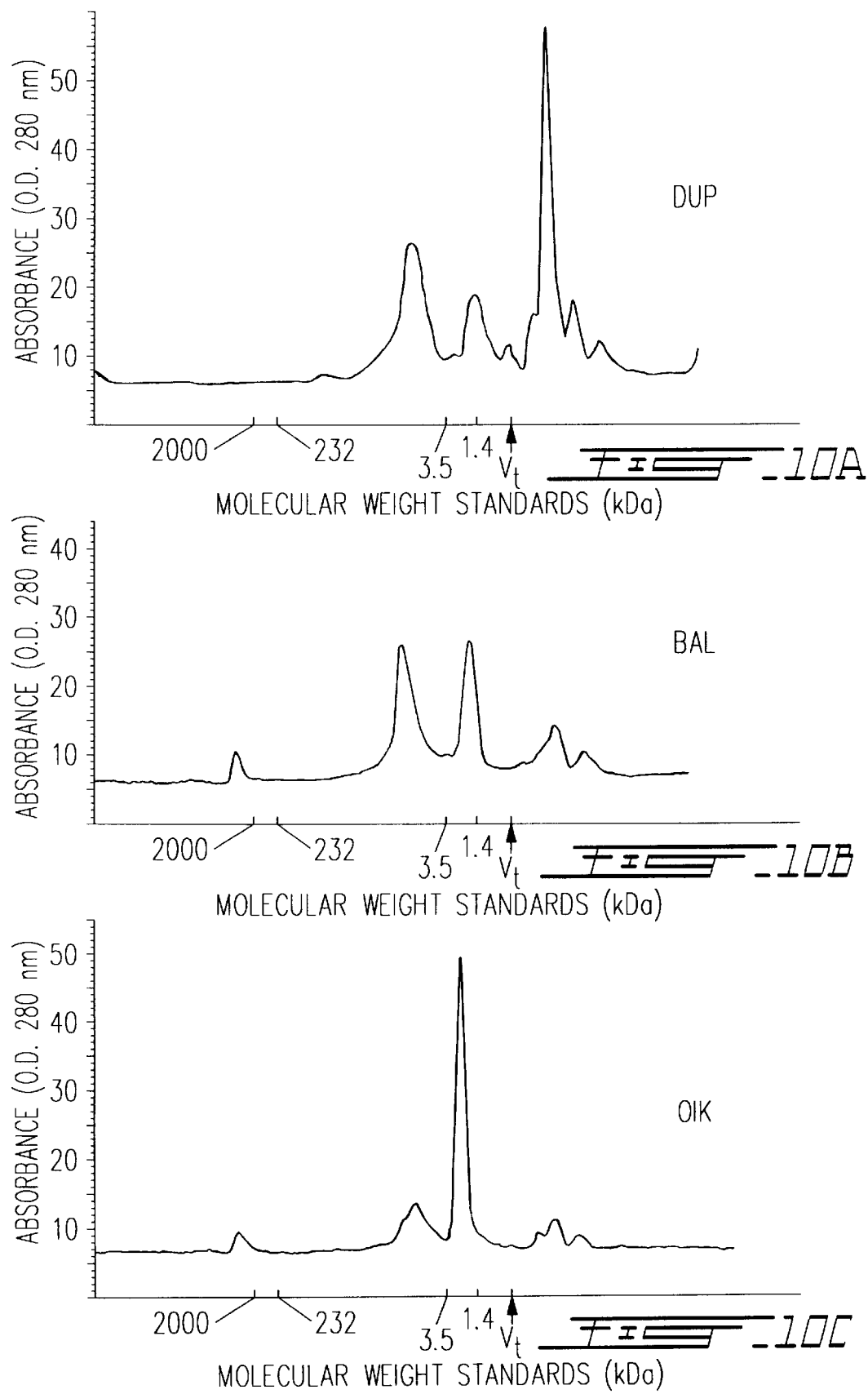

EXTRACTS OF SHARK CARTILAGE HAVING ANTI-COLLAGENOLYTIC, ANTI-INFLAMMATORY, ANTI-ANGIOGENIC AND ANTI-TUMORAL ACTIVITIES; PROCESS OF MAKING, METHODS OF USING AND COMPOSITIONS THEREOF

CROSS REFERENCE TO EARLIER FILED APPLICATION

This application is a continuation-in-part of application Ser. No. 384,555 filed Feb.3, 1995, now U.S. Pat. No. 5,618,925 issued Apr. 8, 1997, which is a continuation-in-part of application Ser. No. 234,019 filed Apr. 28, 1994 now abandoned.

BACKGROUND OF THE INVENTION

Cartilage is an avascularized tissue and has been studied as a potential candidate containing anti-angiogenic factors. It is also a tissue which is relatively resistant to tumor development. The tumor associated with cartilage, chondrosarcoma, is the least vascularized of solid tumors. Angiogenesis is one of the important factors in the development of a tumor. Discrete solid tumoral masses appear if the tumor cells can provoke the adjacent vascular network to expand to supply their nutritional needs. Therefore, the factors involved in the stimulation of angiogenesis have been studied for their role in the development of tumor and anti-angiogenic factors as well as drugs having an angiogenic inhibitory activity have been also investigated as tools for controlling the growth or for effecting regression of tumors.

It has been discovered that scapular cartilage in calves contains a substance that inhibits the vascularization of solid tumors (Langer et al., 1976). Because of its encouraging potential as anti-tumor agent, sources of greater supply of cartilage have been looked for.

Sharks are animals being a potential source of this kind of angiogenesis inhibitor because their endoskeleton is composed entirely of cartilage (6% of their body weight versus 0.6% in calves). Sharks have also as an interesting characteristic a low propensity to developing tumors. Many hypotheses have been elaborated to explain this low probability of developing tumors in sharks. Marchalonis et al. (1990) have shown IgM antibodies able to readily attack any aggressing agent. McKinney et al. (1990) have shown that sharks have macrophages capable of differentiating normal cells from neoplastic cells and of destroying the latter. Rosen and Woodhead (1980) have postulated that the rarity of tumors in elasmobranchs (a group to which pertain sharks and rays) might be due to the high ionic strength of their tissues, which is equivalent to a high body temperature. In these conditions, these authors believe that the immune system exerts a close to 100% immunological surveillance. Moore et al. (1993) have discovered that sharks produce an aminosterol having antibacterial and antiprotozoal properties. Finally, Lee and Langer (1983) and Folkman and Klagsbrun (1987) have shown that sharks produce a substance which inhibits neovascularization. Lee and Langer (op.cit.) have isolated this substance by extracting it from shark cartilage in denaturing conditions (guanidine extraction). This process of extraction is however very long (41 days) might generate extracts having denatured factors and the yield of active components is far from excellent. While the active substance isolated from calves has a molecular weight of about 16 kilodaltons (kd), the same group of researchers have not given a precise molecular weight to the one retrieved in sharks. This substance is only defined has having a molecular weight higher than 3500 daltons. Oikawa et al. (1990) have applied the same method of extraction as the one described by Lee and Langer, but of a much shorter duration (2 days instead of 41 days). The anti-angiogenic substance isolated from shark cartilage by Oikawa et al. is restricted to a molecule having a molecular weight ranging from 1000 to 10,000 daltons. Schinitsky (U.S. Pat. No. 4,473,551) has described a water extract of crude powdered shark cartilage which fraction of more than 100,000 Daltons has an anti-inflammatory activity alone or in combination with glucosamine. No suggestion of a component of this extract having an anti-angiogenic or anti-tumor activity is made in this patent. Kuetner et al. (U.S. Pat. No. 4,746,729) have isolated a polymorphonuclear neutrophil (PMN) elastase inhibitor from bovine cartilage. This inhibitor has been obtained from an aqueous extract of cartilage from which molecules of a molecular weight of less than 50,000 Daltons have been retained. Fractionation on SEPHACRYL S-200™ (cross-linked co-polymer of allyl dextran and N,N methylene bisacrylamide) has given numerous fractions from which those of 10–40 kD have been pooled after they have demonstrated an anti-elastase activity. The active component has an isoelectric point of 9.5 and might have a molecular weight of about 15,000 Daltons. Kuetner et al. (U.S. Pat. No. 4,042,457) have also shown that bovine cartilage has a component of a molecular weight of less than 50,000 Daltons which has a cell proliferation inhibitory activity without any activity on endothelial cell growth. Balassa et al. (U.S. Pat. No. 4,822,607) have obtained a cartilage extract in an aqueous solution, which extract has an anti-tumoral activity. However, we have observed no anti-angiogenic activity in an extract obtained by reproducing Balassa's method. Spilburg et al. (U.S. Pat. No. 4,243,582) have isolated two glycoproteins of molecular weight of 65 KD and of pI 3.8 from bovine cartilage (guanidine-extraction) which show anti-trypsin activity and an endothelial cell growth inhibitory activity.

Calf and shark cartilage contain many biological activities such as pro-inflammatory activity, anti-inflammatory activity, anti-angiogenic activity, lysozyme activity, cell growth-promoting activity, inhibitory activity against types I and IV collagenase, elastase, and other proteases like trypsin, chymotrypsin and plasmin. However, nobody has yet obtained a cartilage extract which comprise a pool of clinically valuable activities.

Shark cartilage anti-angiogenic component(s) have been generally tested in rabbit corneal pocket assay or in chick chorioallantoic membrane (CAM) assay. Up to date, whole powdered cartilage has been tested directly on tumors in vivo, on human melanoma xenograft implanted in nude mice (U.S. Pat. No. 5,075,112), as well as tested in CAM tests for its anti-angiogenic effect. Even though an anti-tumoral effect has been assigned to cartilage extracts, this effect has most often been attributed to the anti-angiogenic component which deprives the tumor of blood supply. Up to now, there is no evidence that a shark cartilage has a direct effect on tumor cell proliferation.

A few methods of obtaining a shark cartilage extracts and fractions are already known. Some of them produce a powdered crude cartilage without any extraction (U.S. Pat. No. 5,075,112). Others use denaturing agents like guanidine (U.S. Pat. No. 4,243,582). Others perform a pre-treatment of cartilage by way of an enzymatic digestion to get rid of any muscular, nervous or vascular structures surrounding the cartilage, which pre-treatment step is followed by the elimination of fats in organic solvents, and then the active components are extracted in an aqueous phase. (Balassa et al. U.S. Pat. Nos. 3,478,146, 4,350,682, 4,656,137 and 4,822,607). The effect of such pre-treatment on the preservation of the integrity of the biologically active cartilage components is not known. If too extensive, an enzyme digestion may hydrolyse active proteic components Balassa's method does not include a fractionation step which would enrich an extract in active components. Others simply produce aqueous extracts (in water (U.S. Pat. No. 4,473,551) or salt solutions (U.S. Pat. No. 4,746,729)) of cartilage by eliminating the unsolubilized material. Among the latter, specific fractions of specific molecular weights have been particularly retained for further study and purification (see discussion above).

The above-cited methods have several drawbacks. They may denature some valuable components. When such might not be the case, they have the disadvantage of being too lenghty to be of a practical purpose. Moreover, the lenghty methods do not necessarily yield sufficient amounts of active components, and among the recovered components, some are not recovered at all or in unsufficient yield to show detectable activity or some have been disregarded by focusing on the obtention of specific activities.

Angiogenesis is not only involved in cancer development. Many diseases or conditions affecting different physiological systems (indicated in parentheses) are angiogenesis-dependent among which the following examples: arthritis and atherosclerotic plaques (bone and ligaments), diabetic retinopathy, neovascular glaucoma, trachoma and corneal graft neovascularization (eye), psoriasis, scleroderma, hemangioma and hypertrophic scarring (skin), vascular adhesions and angiofibroma (blood system). Therefore, any new and potent anti-angiogenic "factor" could find a use in the treatment of these diseases as well as in cancer therapy. Moreover, since many of the above—mentioned diseases and conditions also have an inflammatory component, any new and potent anti-inflammatory "factor" could find a use in the treatment of these diseases and conditions as well as of any other inflammatory diseases or conditions. Furthermore, since proteases like collagenases are involved in a diversity of diseases and conditions like cancer and premature aging because of its collagen degrading activity, a new and potent anti-collagenolytic "factor" could find a use in the treatment of diseases or conditions having a collagenolytic component. Because angiogenesis, inflammation and proteases like collagenases may be encountered alone or in combination in a large variety of diseases or conditions, a product capable of antagonizing at least all these activities without affecting normal body functions would be of a great therapeutic value.

STATEMENT OF THE INVENTION

The present invention provides a new method of producing cartilage extracts which have the advantage of containing a multiplicity of therapeutically valuable activities. Among those, anti-angiogenic, anti-inflammatory, anti-collagenolytic, in vivo anti-tumor proliferating and direct in vitro anti-tumor proliferating activities have been confirmed to be present in satisfying concentrations in a shark cartilage extract. Other activities await identification or confirmation. The effect measured in tumor cell lines was indicating that beside a direct anti-tumor proliferating activities, a cytotoxic activity appears to be present. All activities have been obtained in a liquid extract of shark cartilage, and some of them have been obtained or verified in a solid extract of the same.

The present invention relates to a new process for the obtention of a liquid extract of cartilage having a substantial portion of the biologically active hydrosoluble components present in intact cartilage, which comprises the following steps:

a) homogenizing the cartilage in an aqueous solution in conditions compatible with the preservation of the integrity of said biologically active components until the cartilage is reduced to particles whose size is lower than or equal to about 500 $\mu$m, resulting in a mixture of particles and of a crude liquid extract having said biologically active components;

b) centrifuging said homogenate to separate particles from the crude liquid extract; and c) further separating the crude liquid extract so as to obtain a final liquid extract containing cartilage molecules having a molecular weight lower than or equal to about 500 Kilodaltons.

This new process has the advantage of being easy to perform and efficient. High yields of cartilage extract have been obtained, which extract, particularly obtained from shark cartilage, contains at least all the above-mentioned biological activities. It is preferably performed at cold temperature (about 0 to 10° C.), in non-denaturing conditions (preferably in pure water), at a near neutral pH (about 6 to 8) to maximize the probability of recovering compounds of unknown physico-chemical characteristics. According to this process, cartilage components can be extracted in a low volume of solution (as low as 1 L for 1 Kg of cartilage), and after a short period of homogenization (as short as 10 to 15 minutes). For the recovery of a solid extract, the same process is used, except that the pellet is recovered and lyophilized, disregarding the supernatant.

This invention relates to cartilage extracts, particularly to extracts providing from elasmobranch species, more particularly from shark. The solid extract has shown activity. It may contain collagen and non-hydrosoluble components. It may also contain a residual activity of what was extracted in the total liquid extract. The total liquid extract is very rich in activity. It can be used as such or it can be concentrated. A concentration step which favorizes the maintenance of biological activities has been priviledged. Recourse to methods which could deteriorate the active components like heat-evaporation has been avoided by caution. Ultrafiltration on a membrane having a molecular weight cut-off value of about 1 KDa has been used to concentrate the liquid extract of this invention. As a result, a concentrated extract containing molecules of a molecular weight comprised between about 1 and about 500 KDa was obtained and tested. The total liquid extract (0 to 500 KDa) has been further fractionated to characterize the active components thereof. Numerous fractions have been obtained by different methods. Some of them tested on tumor cell lines have been grossly characterized by their molecular weight and isoelectric point. Others have been assigned an activity, particularly anti-collagenolytic or anti-angiogenic activities. These fractions await complete characterization and identification. Therefore, valuable activities are recovered in a total liquid extract and fractions thereof, which may be advantageously used. In lieu of administering high amounts of powdered cartilage, a more acceptable and enriched extract may now be administered.

The present invention also relates to any therapeutic or cosmetic compositions comprising as an active ingredient one of the above-cartilage extracts. Most interest has been drawn to topical compositions for use in dermatology and cosmetology. This interest comes from the observed activities of the cartilage extracts. In this respect, the observed anti-collagenolytic and anti-inflammatory activities, and the antagonistic effect of cellular differenciation mediated by the induction of Protein Kinase C in keratinocytes have been considered as opening avenues to the use of the shark cartilage extracts in compositions and methods for the reduction of inflammation, the regulation of wrinkle or skin atrophy, the retardation of premature aging, the reduction of acne, the improvement of skin barrier function, the reduction of inflammation or irritation and a skin soothing effect. Such methods are under the scope of this invention. Furthermore, since the shark cartilage liquid extract has been successfully tested in cancer, arthritis, psoriasis and acne cases, compositions and methods for treating diseases or conditions having one or more components selected from the group consisting of tumor proliferation, angiogenesis, inflammation and collagenolysis, are under the scope of this invention.

DESCRIPTION OF THE PRESENT INVENTION

The present invention will be more readily understood by way of the specific embodiments shown in the appended figures, which purpose is to illustrate the invention rather than to limit its scope:

BRIEF DESCRIPTION OF THE FIGURES

FIG. 3a depicts a liver section from a control animal. The cytoplasm and nucleii of parenchymal cells show a normal appearance.

FIG. 4a depicts a section through the cortex of a kidney of a control animal. All the tubular cells appear normal with clear and well delimited cytoplasm. The tubular lumen are empty.

FIG. 5a depicts a secton through a lung of a control rat. The wall of a bronchiole (B) as well as the alveoli (A) appear intact with well delimited epithelial cells.

FIG. 6a depicts a DMBA-induced mammary tumor in a control rat. Blood vessels are numerous and some of them (V) are large.

FIGS. 10a), 10b) and 10c) show a FPLC migration pattern of three different extracts of shark cartilage. In FIG 10a, DUP stands for a cartilage liquid extract according to this invention. In FIGS. 10b) and 10c), BAL and OIK stand for extracts of the prior art, Balassa et al. and Oikawa et al., respectively.

In a specific embodiment, cartilage has been obtained from healthy sharks Black Spiny Dog Fish and Common Spiny Dog Fish. Any muscular and connective tissue has been removed by scraping with ethanol-treated scalpels and scissors. The cartilage was then vacuum-packed in plastic bags and frozen to −20° C. for further use. In the present process any source of cartilage may be used. We have chosen shark cartilage for reasons enunciated in the BACKGROUND section. It is believed that starting from elasmobranch cartilage (which includes sharks and rays as animal species of this group), near equivalent products would be obtained. The products will most probably be different if mammalian source of cartilage are used.

Figure 15:
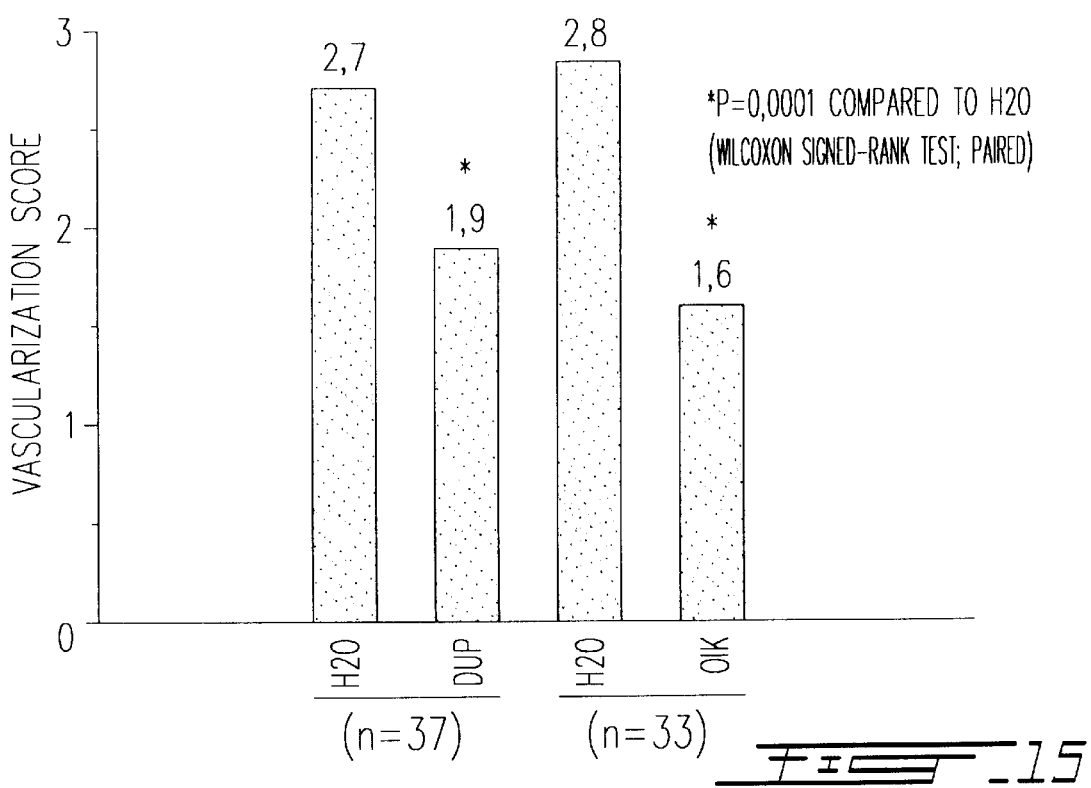
FIG. 15 shows the results of CAM-tests performed with the total liquid extract of our invention (DUP) when compared to a sample providing from an equal quantity of dry matter weight of a product made by the process of Oikawa (OIK).

Any variation in the preparation of cartilage prior to its extraction may be used as long as it does not substantially affect the activity of the product of interest (a total liquid extract or a particular fraction thereof, for example). Some active components may resist to proteolytic digestion as taught by Balassa et al. (U.S. Pat No. 4,822,607) to rid the cartilage of any surrounding tissues, while others may not resist to such treatment. One of the activities which do not appear to resist to such pre-treatment is the anti-angiogenic activity (FIG. 15). Therefore if one wants to produce a liquid extract containing as much as possible of all the hydrosoluble active components to which are assigned separate activities, such a digestion step should be avoided or carefully monitored to prevent extensive hydrolysis or proteolysis.

PREPARATION OF LYOPHILIZED CARTILAGE

Clean cartilage was used fresh or thawed to 4° C. Cartilage was then passed numerous times (more particularly three times) through the pores of an ethanol-treated meat chopper together with a adequate volume of water (an equal quantity (weight/volume) is about a minimal volume but can be increased without bearing any effect on the yield of recovery of valuable components). A low volume is preferred since it is more convenient to manipulate than unnecessary high volumes, from a practical point of view. In the practice, water has been purified by inverse osmosis and filtration on a 0.1 µm filter. Many aqueous solutions (containing salts, for example) could be used in lieu of water. When recovery of a plurality of hydrosoluble activities is contemplated, working at a near neutral pH and non-denaturing conditions are preferred to avoid lysis or denaturation of some of the cartilage components. The behavior of unknown proteins in aqueous solvents is not predictable; some may be more "comfortable" in an acidic pH, some at a basic pH. Furthermore, some proteins may be extractable in mild denaturing conditions, if such denaturation does not irreversibly affect the re-naturation of these proteins in aqueous solutions. Therefore, taking all these factors in consideration, performing a process of extraction of cartilage active components in pure water has been shown to be a judicious choice to recover with a very good yield, components having an unknown structure and behaviour.

The blend cartilage/water was then made homogenized by an agitation at a maximal speed in an kitchen blender at about 4° C. during ten minutes. Of course, the speed of the agitation as well as the volume of aqueous solution may influence the time of extraction. Therefore, a reasonable range of homogenization time could be as low as about 10 minutes to as high as 24 hours, preferably between about 10 and 60 minutes. The temperature should be maintained to below about 10° C., to avoid any degradation of active components by endogenous enzymes, when no enzyme inhibitors are used. Ideally, a temperature close to 0° C. should be sought. Since normally such experimentation is made in a cold room, wherein the temperature can be maintained between 4 and 10° C., this range of temperature is acceptable in the present process. For sake of clarity and brevity, the terms "about 4° C." is hereinbelow used to designate this acceptable range of temperatures.

A liquefaction of this homogenate can be further obtained by submitting the latter to Polytron disintegrator during 10 minutes at 40° C. if the blender did not sufficiently reduce the size of the particles. Alternatively, the blend can be simply homogenized in a more performing a blender-desintegrator which, in our hands, saved the 10 min liquefaction step. At the end of the completed homogenisation step, residual particle size is less than about 500 µm. Of course, the same acceptable ranges of time and temperature discussed for the obtention of the first grinded cartilage equally apply. The size of the particles after homogenization does not need to be very small. Therefore, the need to pulverize the cartilage before extraction can be avoided. Indeed, pulverization of cartilage in the form of a powder before aqueous extraction may denature valuable activities, when such pulverization is performed in a freeze-dry state or in a heat-dry state.

The homogenate was centrifuged at 13,600×g during 15 minutes at 4° C., which step is one way to separate quickly and efficiently a supernatant from a pellet. Variation and adjustment of these parameters are well within the knowledge of the skilled artisan, merely depending on the volume of homogenate and of the used equipment.

The resulting pellet was lyophilized for 24 to 48 hours. This first fraction will hereinbelow be defined as the lyophilizate or a solid extract.

The supernatant can be filtered on a 24 µm Whatman filter, if necessary, to get rid of particles susceptible to affect the performance of an ultrafiltration column. The filtrated material was then ultrafiltrated at about 4° C. on an tangential flow filtration column having a porosity of about 500 000 Daltons, which allows a first crude permeate to be obtained comprising hydrosoluble molecules of a molecular weight comprised between 0 and about 500 KDa. This crude permeating extract was sterile filtered on 0.22 µm filter, and aliquoted in sterile bottles for further use. This fraction will be further referred to as the crude permeate or the total liquid extract.

An alternative, higher performing centrifuging procedure has been developed to obtain the pellet and the supernatant. The step of centrifuging at 13600×g for 15 minutes followed by a gross filtration on Whatman filters has been replaced by a centrifugation in a CEPA centrifuge equipped with a nylon pocket of a porosity of 30 µM, at 3000–4000×g. A 25 kg/25 L preparation can be centrifuged in that manner within 30 minutes and provide 29 liters of supernatant. The aqueous volume obtained is higher than the starting volume of water, suggesting that a part of the water content of the cartilage itself has been harvested. The lyophilizate and the total liquid extract may have the following approximate composition which grossly takes into account the variations observed from batch to batch, and when using different material:

Lyophilizate
  Lipids 7.35%[1]
  Proteins 46.2%[2]
  Humidity 20.4%
  Sodium 4.16 mg/g[3]
  Potassium 2.64 mg/g Calcium 114 mg/g
Magnesium 1.49 mg/g
Zinc and iron traces
Total Liquid Extract
Lipids 0.10–0.20%[1]
Proteins 8–25 mg/Ml[2]
Humidity 97–99%
Sodium 30–220 mg/100 g[3]
Potassium 30–40 mg/100 g
Calcium 2.0 mg/100 g
Magnesium 1.1 mg/100 g
Zinc and iron traces

[1,2] Measured following directives published in AOAC Official (1984) sections 16.219–220 and 2.055, respectively;
[3] Measured following the SAA procedure.

The protein content is evaluated by the Kjeldahl method, which indeed measures organic nitrogen (N). Organic nitrogen is converted to equivalent protein by using the following equation:

$$\text{Proteic content (mg/mL)} = \frac{\% N \times 6.25}{100}$$

Carbohydrates being not detectable, one can presume that they are in one or another extract but under the form of proteoglycanes and/or mucopolysaccharides. It is possible that these compounds are included in the measured level of humidity. The lyophilizate contains an unexpected level of humidity which was measured by the OH- groups. Since the 20% water content is close to the percentage of carbohydrates normally retrieved in cartilage while the humidity of a lyophilizate should be close to 0%, this hypothesis remains to be verified.

Sterility has been controlled, applying USP XXIII specifications by:

1) Laboratoire de génie sanitaire du Québec Inc. 1090, l'Escarbot, Centre Industriel St-Malo, Québec G1N 4J4; and
2) Northview Laboratories Inc. 1880, Holste Road, Northbrook, Ill., 60062 U.S.A.

FDA registration no. 14-18028
Activity assays
Lyophilizate
In vitro assays

These assays have been conducted on the hormono-dependent cancer cell lines MCF-7 and ZR75-1 (ATCC (R) numbers 22-HTB and 1500-CRL, respectively).

ZR75-1 cells
BASAL RPMI medium 52 g RPMI 1640 without phenol red (Sigma R8755), 17.875 g Hepes (free acid; Sigma H0763), 0.55 g sodium pyruvate (Sigma P5280) and 10 g NaHCO$_3$ were mixed in 5 L of pure water and made pH 7.40 with NaOH.

If not used immediately, this solution must be protected from light to preserve photolabile substances. This solution was filtered, distributed in 500 mL sterile bottles and stored at 4° C. for a maximal period of three months.

Cell culture maintenance medium

Basal RPMI medium was supplemented with 10% (v/v) FBS (fetal bovine serum), 100 U penicillin G/50 μg streptomycin sulfate (sigma P0906)/ml medium, 2 mM L-Glutamine (Sigma G1517) and 1 nM E$_2$ (β-estradiol Sigma E8875).

Experimental medium

Basal RPMI medium was supplemented with 5% FBSA (fetal bovine serum adsorbed on dextran-charcoal), 2 mM L-Glutamine, 100 U penicillin G/50 μg streptomycin sulfate/ml medium and 50 ng/mL insulin (Sigma). To this medium was added increasing concentrations of the above-described lyophilizate as well as different concentrations of estradiol ($10^{-12 \text{ to } -5}$ M)

MCF-7 cells
BASAL DME-F12 medium

DME-F12 medium (without bicarbonate and without red phenol; Sigma) was reconstituted following the manufacturer's directives in pure water. For one liter, 1.2 g of sodium bicarbonate was added and the pH made to 7.40 with NaOH/HCl. This solution was filtered, distributed in 500 mL sterile bottles and stored at 4° C. for a maximal period of three months.

Cell culture maintenance medium

Basal DME-F12 medium was supplemented with 10% (v/v) FBS (fetal bovine serum), 100 U penicillin G/50 μg streptomycin sulfate/ml medium, 2 mM L-Glutamine (Sigma) and 1 nM E$_2$ (estradiol).

Experimental medium

Basal DME-F12 medium was supplemented with 5% FBSA (fetal bovine serum adsorbed on dextran-charcoal), 2 mM L-Glutamine, 100 U penicillin G/50 μg streptomycin sulfate/ml medium and 50 ng/mL insulin (Sigma). As described for the ZR75-1 cells, lyophilizate and estradiol were added at the same concentrations.

Preparation of FBSA

Fetal bovine serum was mixed with 1% (w/v) charcoal (carbon decolorizing alkaline). A solution of dextran T70 was added to the charcoal-serum solution to achieve a concentration of 0.1% (w/v). The mixture was agitated overnight at 4° C. After centrifugation at 4° C. for 30 minutes at 10,000×g, the serum was decanted, mixed again with the same proportions of charcoal and dextran, agitated at room temperature for three hours and recentrifuged. The serum was then heat-inactivated at 56° C. for 20 minutes, sterile filtered and aliquoted in sterile conical Falcon tubes.

ZR75-1 and MCF-7 cells were grown to reach a density of population of 20000 cells/well on 24-well plaques or 150 000 cells/well on 6-well plaques, and treated in the presence or absence of different concentrations of lyophilizate as prepared above. To this effect, the lyophilizate is resuspended in culture medium and sterile filtered, so that hydrosoluble components thereof are recovered and tested. All experiments have been performed in triplicates. Culture media have been withdrawn and replaced by fresh media every two days. Cells were grown in an incubator under a constantly humidified atmosphere containing 5% CO$_2$, at 37° C., for 17, 7, 3 or 3 days, corresponding to the first, second, third or fourth experiment, respectively. Cell growth inhibition was measured by direct counting of the cells or by measuring the total DNA content of a well.

|  | Cell Inhibition (%) | |
| --- | --- | --- |
| Concentration of lyophilizate | MCF-7 | ZR75-1 |
| 1$^{st}$ experiment: 17 days | | |
| 1 mg/mL | 1.5 | 2.00 |
| 5 mg/mL | 14.33 | 33.6 |
| 10 mg/mL | 62.66 | 90.8 |
| 2$^{nd}$ experiment: 7 days | | |
| 1 mg/mL | 3.73 | 0.97 |
| 5 mg/mL | 15.7 | 29.00 |
| 10 mg/mL | 68.37 | 66.00 |

-continued

| Concentration of lyophilizate | Cell Inhibition (%) | |
|---|---|---|
| | MCF-7 | ZR75-1 |
| 3rd experiment: 3 days | | |
| 50 mg/mL | 95.8 | 95.00 |
| 100 mg/mL | 94.6 | 98.00 |
| 4th experiment: 3 days | | |
| 10 mg/mL | 34.4 | 51.5 |
| 20 mg/mL | 62.5 | 70.5 |
| 50 mg/mL | 95.8 | 95 |
| 100 mg/mL | 94.6 | 98 |

The above percentages of inhibition of cell growth demonstrate that the lyophilizate can inhibit in a dose-dependent manner the growth of the cells of these two cell lines.

Figure 1:
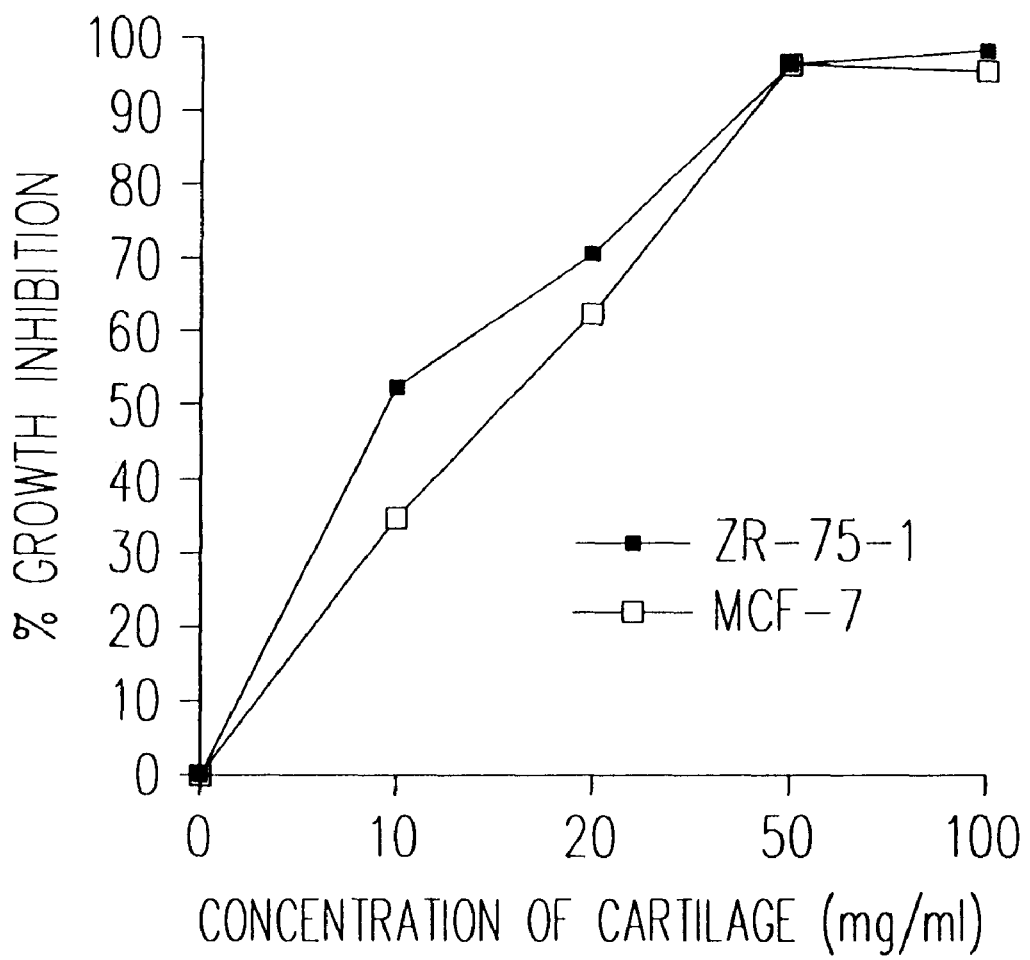
FIG. 1 shows the inhibitory activity of increasing doses of shark cartilage (solid extract) on ZR75-1 and MCF-7 cells.

FIG. 1 shows that doses of 50 and 100 mg/mL of the lyophilizate clearly provoke hypoplasia on these cell lines, after three days of treatment.

Figure 2:
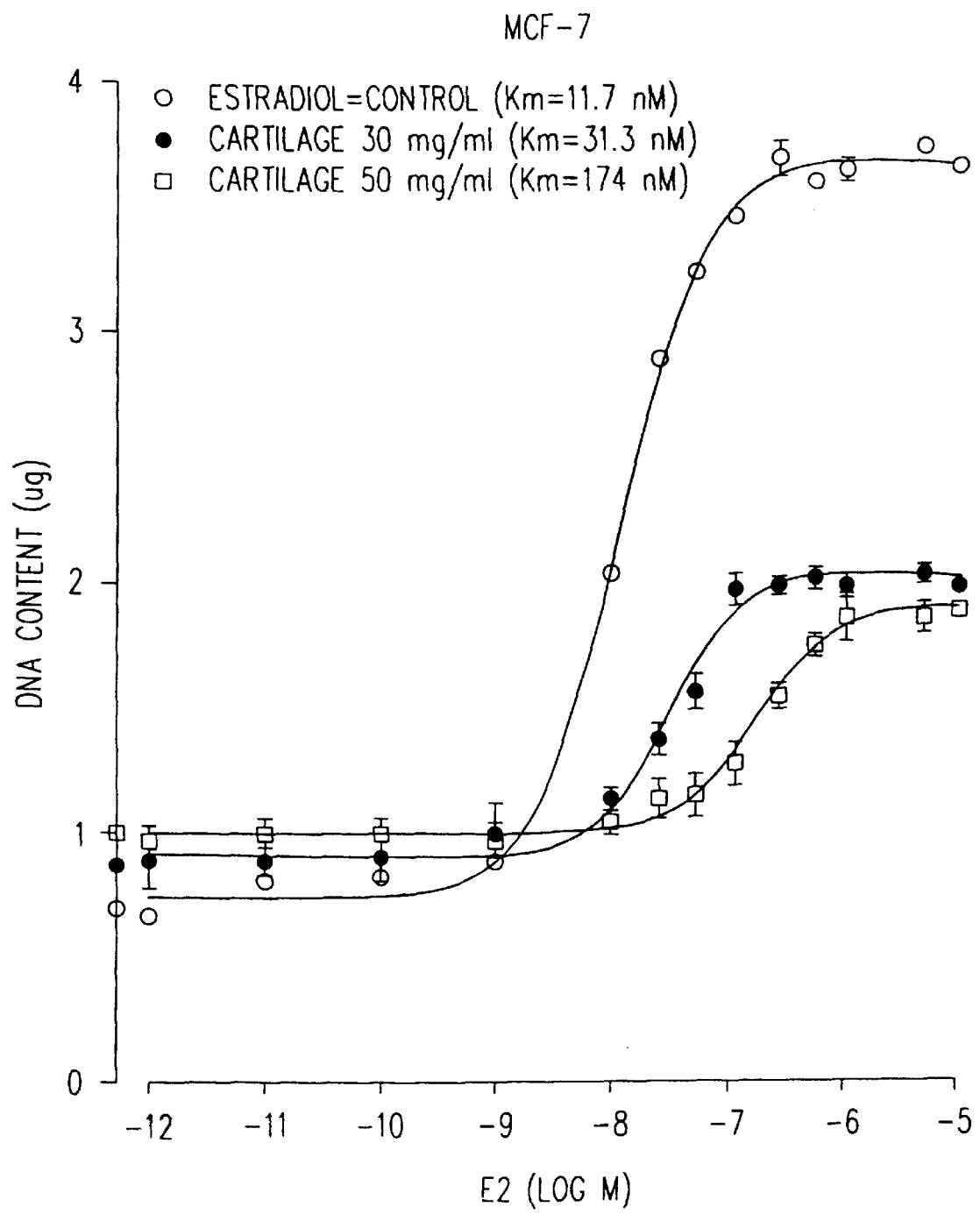
FIG. 2 illustrates dose-response curves of the quantity of MCF-7 cells measured by their DNA content in the presence of increasing concentrations of estradiol with or without two concentrations of cartilage lyophilizate.

FIG. 2 shows that, in the presence of $10^{-12}$ to $10^{-9}$M estradiol, treated cells respond like control cells by being non-stimulated by these hormone dosage rates. However, above 1 nM, control cells are strongly stimulated, and concentration of DNA reach 3.75 ug in the presence of $10^7$M estradiol (versus 0.69 ug in control without estradiol). In cells treated with 30 and 50 mg/mL of lyophilizate, DNA measured at the maximal stimulation is 1.9 and 1.8 $\mu$g, respectively FIG. 2 shows that the affinity constant (Km) of the treated cells for estradiol is 3 and 16 times higher (31.3 nM and 174.0 nM) than the value of Km of the control cells (11.7 nM), in the presence of 30 and 50 mg/mL, respectively. This means that higher concentrations of estradiol are necessary to achieve the same growth of the cells when cartilage lyophilized solid extract is present. Therefore, this extract diminishes the maximal response (90% inhibition thereof) and increases the affinity constant of the treated cells to estradiol.

In vivo assays

Four hundred 40 day old female Sprague-Dawley rats (purchased from Charles River Co., St-Constant, Québec) where adapted to their environment for 12 days. At that time, 20 mg DMBA/1 mL corn oil (9, 10-Dimethyl-1, 2-Benzanthracene; purchased from Sigma Chemical Co.) was administered by gavage. Three months after this treatment, 240 rats having developed a mammary breast cancer have been selected and distributed in two groups. The first group consisted of five sub-groups of rats. The rats of the treated groups were given a daily dose of increasing concentrations of the lyophilizate extract in 3 mL of water for eight weeks while the control group received the same volume of water. The second group consisted in four sub-groups of rats. The rats of the treated groups were also given a daily dose of the lyophilizate in 3 mL of water combined with or without the supernatant, for ten weeks while the control group received the same volume of water. Only one sub-group of the second group of rats treated with a concentration of 3000 mg/Kg/day of the lyophilizate and 3 mL of the supernatant was also given an intraperitoneal (i.p.) injection of a smaller dose of the supernatant (about 8 mg of protein in 1 mL of water).

Rats were weighing 151–175 g at the beginning of the two experiments and received food and water ad libitum. The first group of rats had tumors of average diameter of 0.9 cm while the second group of rats had a tumor of average diameter of 0.6 cm.

The results are summarized as follows:

| Daily doses of cartilage extract administered by gavage | % tumor growth inhibition (decrease of tumor diameter vs control) |
|---|---|
| 1st experiment: duration 8 weeks | |
| 500 mg/Kg/day | 2% |
| 1000 mg/Kg/day | 4% |
| 3000 mg/Kg/day | 14% |
| 5000 mg/Kg/day | 15% |
| 2nd experiment: duration 10 weeks | |
| 3000 mg/Kg/day | 12% |
| 3000 mg/Kg/day + 3 mL supernatant | 18% |
| 3000 mg/Kg/day + 3 mL supernatant + 1 mL inj. i.p. supernatant | 20% |

These results demonstrate that the lyophilizate contains an active component which is absorbed in the gastro-intestinal tract and which has an effect on tumor size. This effect might be a direct effect on tumor cells or an anti-angiogenesis mediated effect.

These results also show that the supernatant has an activity which is reflected by a supplementary reduction of tumor size of about 5%.

These results also suggest that the lyophilizate may contain active components that are not hydrosoluble and/or that it may contain residual hydrosoluble. Therefore, in the last eventuality, one may consider that the pellet could be re-extracted in an aqueous solution to recover hydrosoluble components maximally, if the yield can be still improved.

HISTOPATHOLOGY

For evaluating the non-toxicity of the active molecules of the cartilage extract, the animals used in the above in vivo experiments were killed by decapitation and the following tissues were taken for analysis: liver, lung, kidneys, heart, brain, muscle and mammary gland. Fat was taken out of these tissues, after what they were fixated for two days in Bouin fluid. After dehydration in ethanol, the fixated tissues were embedded in paraffin. Sections thereof were obtained and mounted on glass slides, colored with haematoxylin and visualized under microscope.

Figures 3A, 3B:
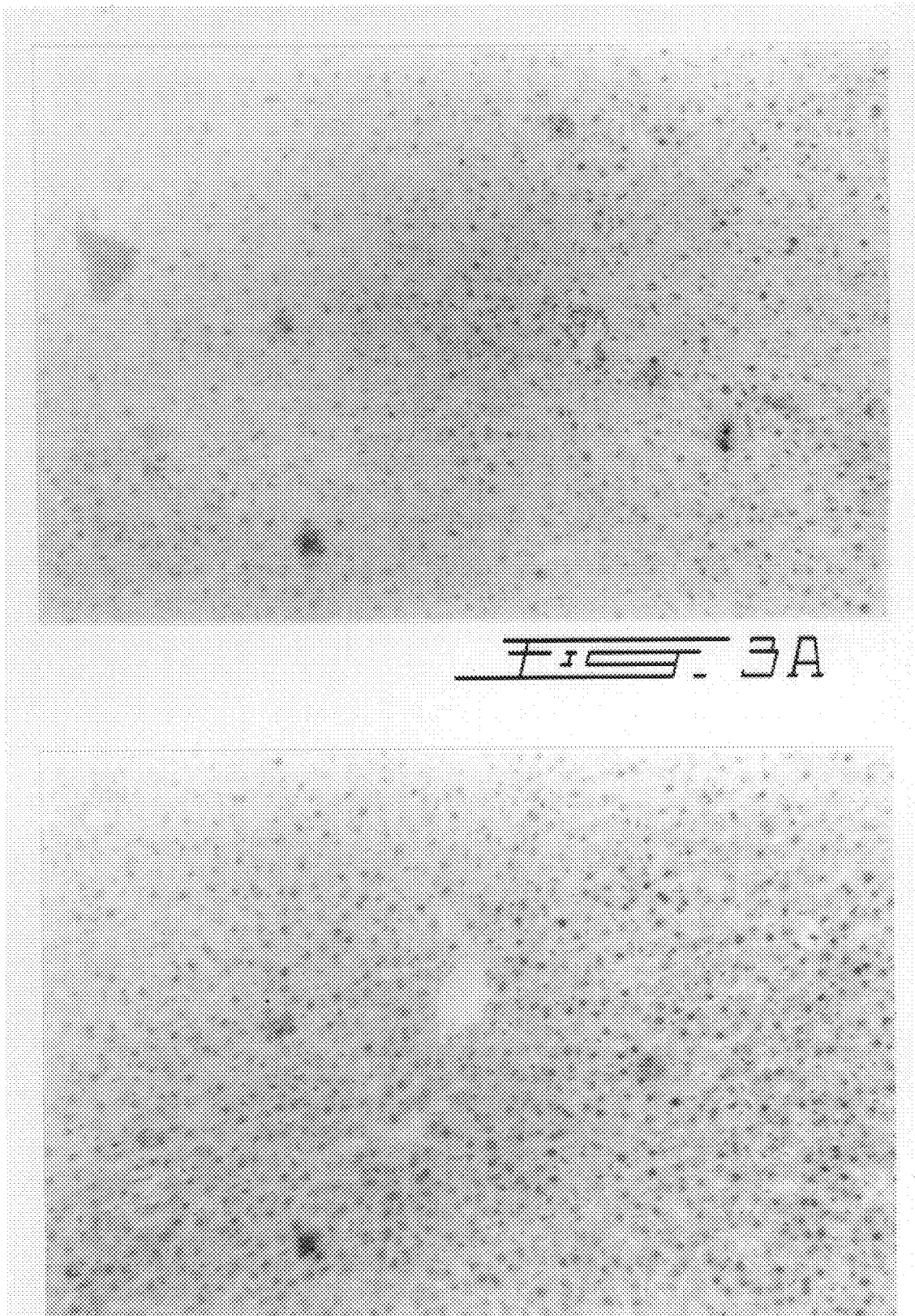
FIGS. 3a) and 3b) show a comparison of liver sections of rats having developed a mammary gland cancer which have been administered by gavage a combination of cartilage lyophilizate and supernatant (FIG. 3b) and those which have been administered only water. Each micrograph (magnification: X200 shows a representative section from either a control (vehicle-treated) adult female rat or an adult female rat treated with the highest dose of shark cartilage extracts administered by intragastric tubing.
FIG. 3b depicts a liver section from a treated animal. The appearance of cytoplasm and nuclei is very similar to that observed in the control animal (see FIG. 3a). No degenerative changes can be observed.
Figure 4A:
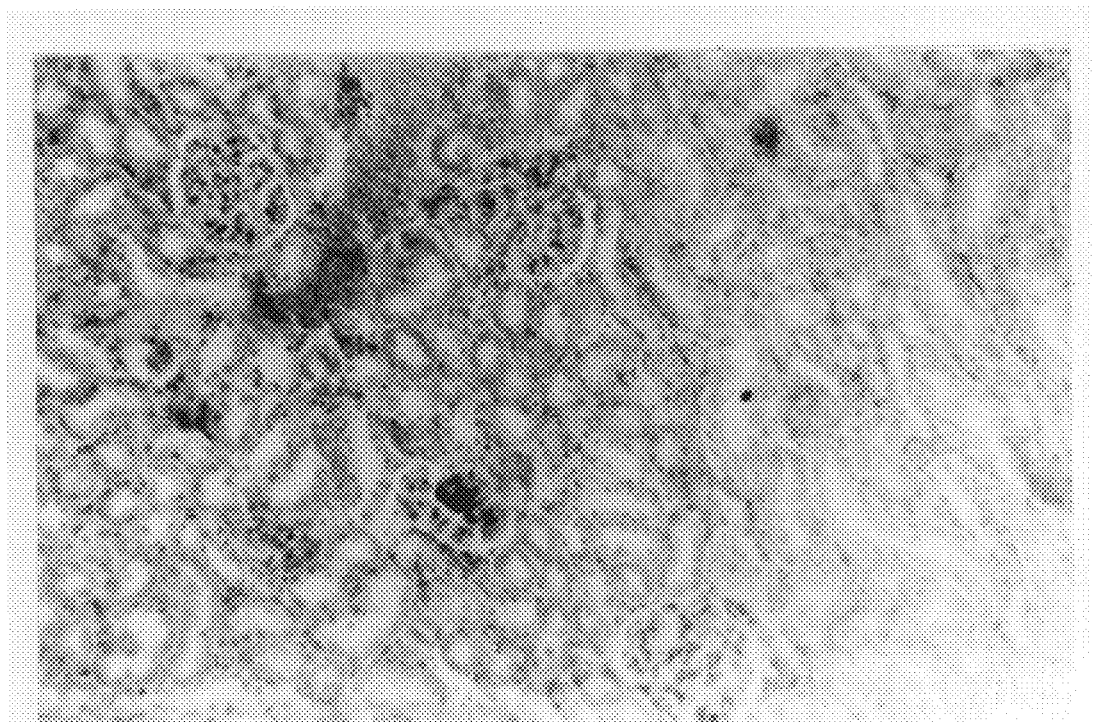
FIGS. 4a) and 4b) show a comparison of kidney sections of rats having developed a mammary gland cancer which have been administered by gavage a combination of cartilage lyophilizate and supernatant and those which have been administered only water.
Figure 4B:
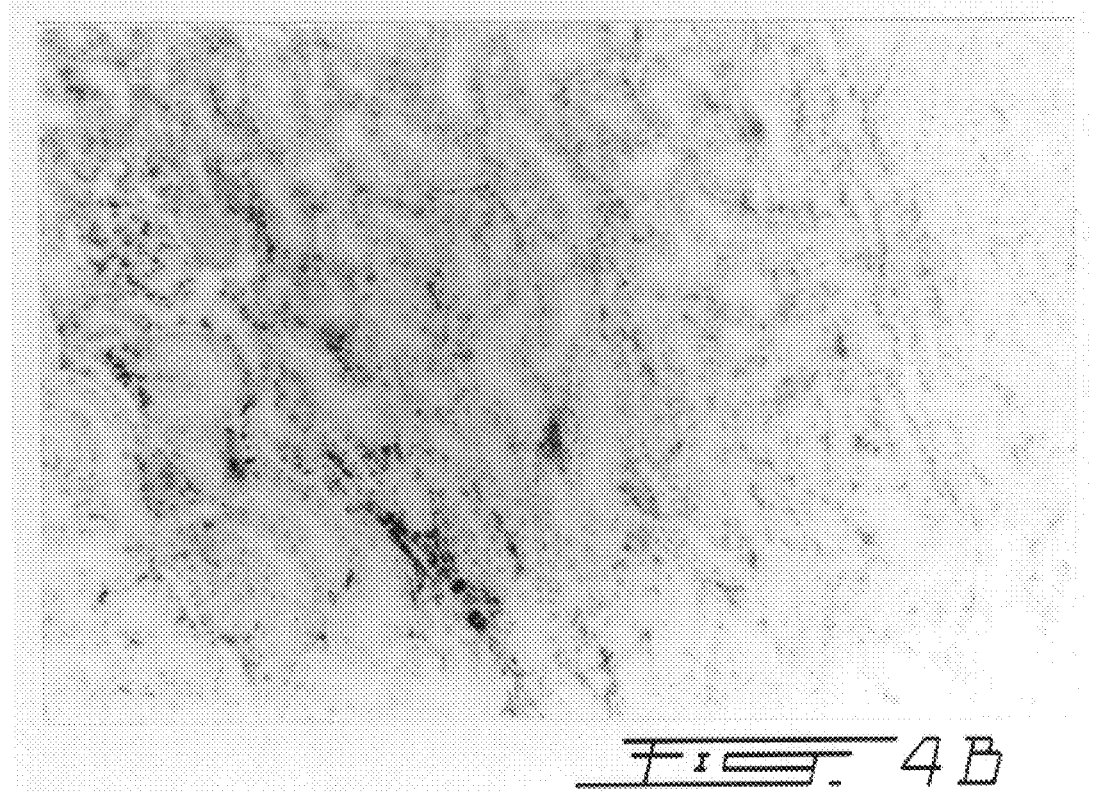
FIG. 4b depicts a section through the cortex of a kidney of a treated animal. The tubular cells have a normal appearance. There is no desquamated cells in the lumen of the tubules. No signs of toxicity can be detected.
Figure 5A:
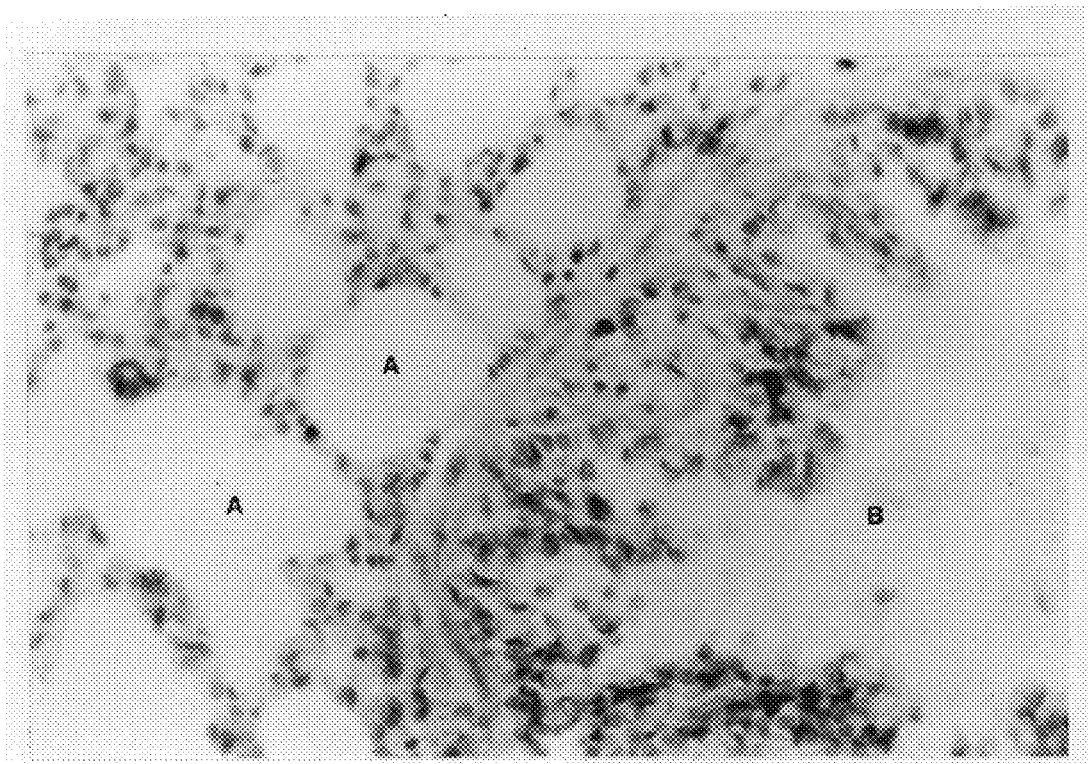
FIGS. 5a) and 5b) show a comparison of lung sections of rats having developed a mammary gland cancer which have been administered by gavage a combination of cartilage lyophilizate and supernatant and those which have been administered only water.
Figure 5B:
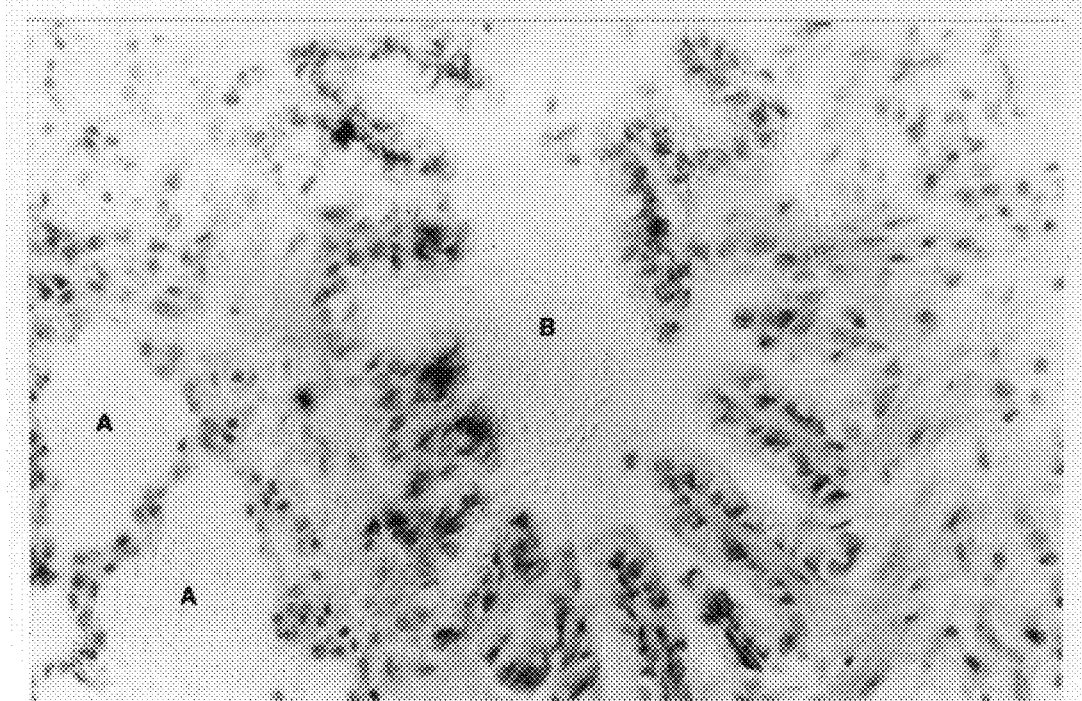
FIG. 5b depicts a section through the lung of a treated animal. The cells of the wall of a bronchiole (B) and alveoli (A) have a normal appearance, being very similar to those observed in control animals (FIG. 5a). The lumen are free of any desquamated cells.

The histological examination revealed that no deleterious effect was visible when using the largest doses of lyophilizate alone (data not shown) or when using the lyophilizate in combination with the supernatant (see FIGS. 3a and b, 4a and b, and 5a and b).

This suggests that the lyophilizate and the supernatant have a selective tumor size regressive activity.

Figure 6A:
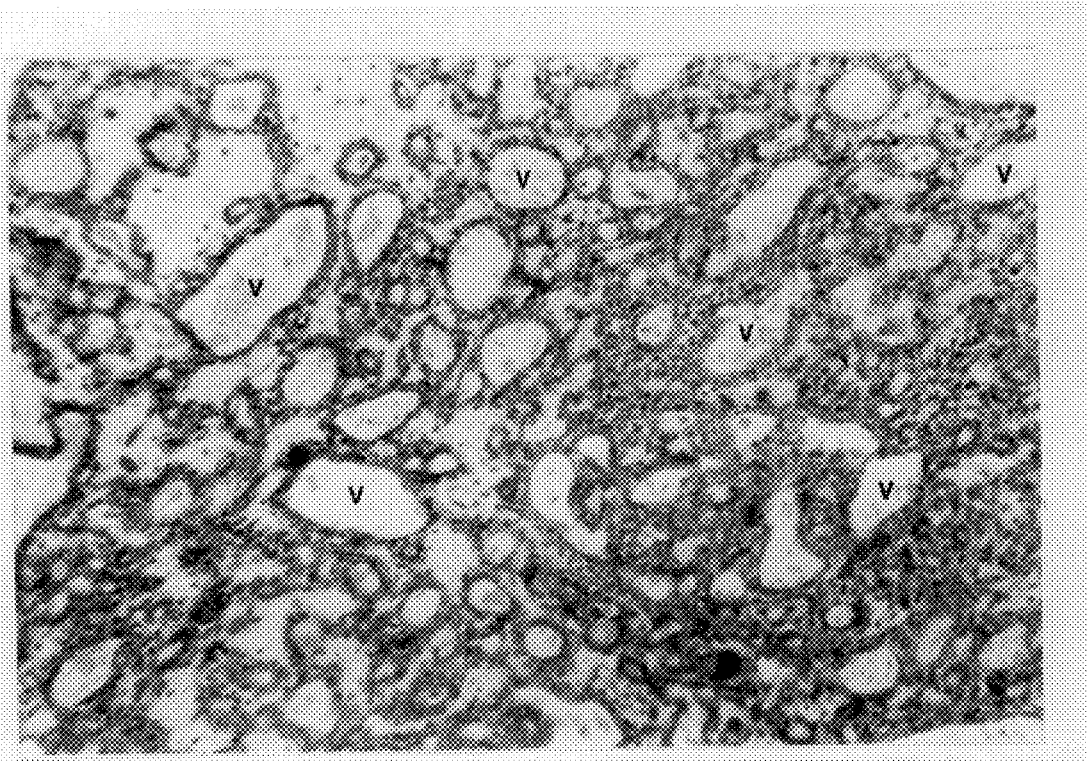
FIGS. 6a) and 6b) show a comparison of mammary gland tumor sections of rats having developed such a tumor which have been administered by gavage a combination of cartilage lyophilizate and supernatant and those which have been administered only water.
Figure 6B:
FIG. 6b depicts a DMBA-induced mammary tumor in a treated rat. There are major histological changes due to the decrease in the number and size of blood vessels (V). This provides the appearance of a more compact tissue. (X120).

In cancerous mammary gland (see FIGS. 6a and b), an important diminution of the area of blood vessels was observed. The anti-angiogenic effect of these active molecules is then confirmed by results as illustrated and summarized in FIG. 7.

Figure 7:
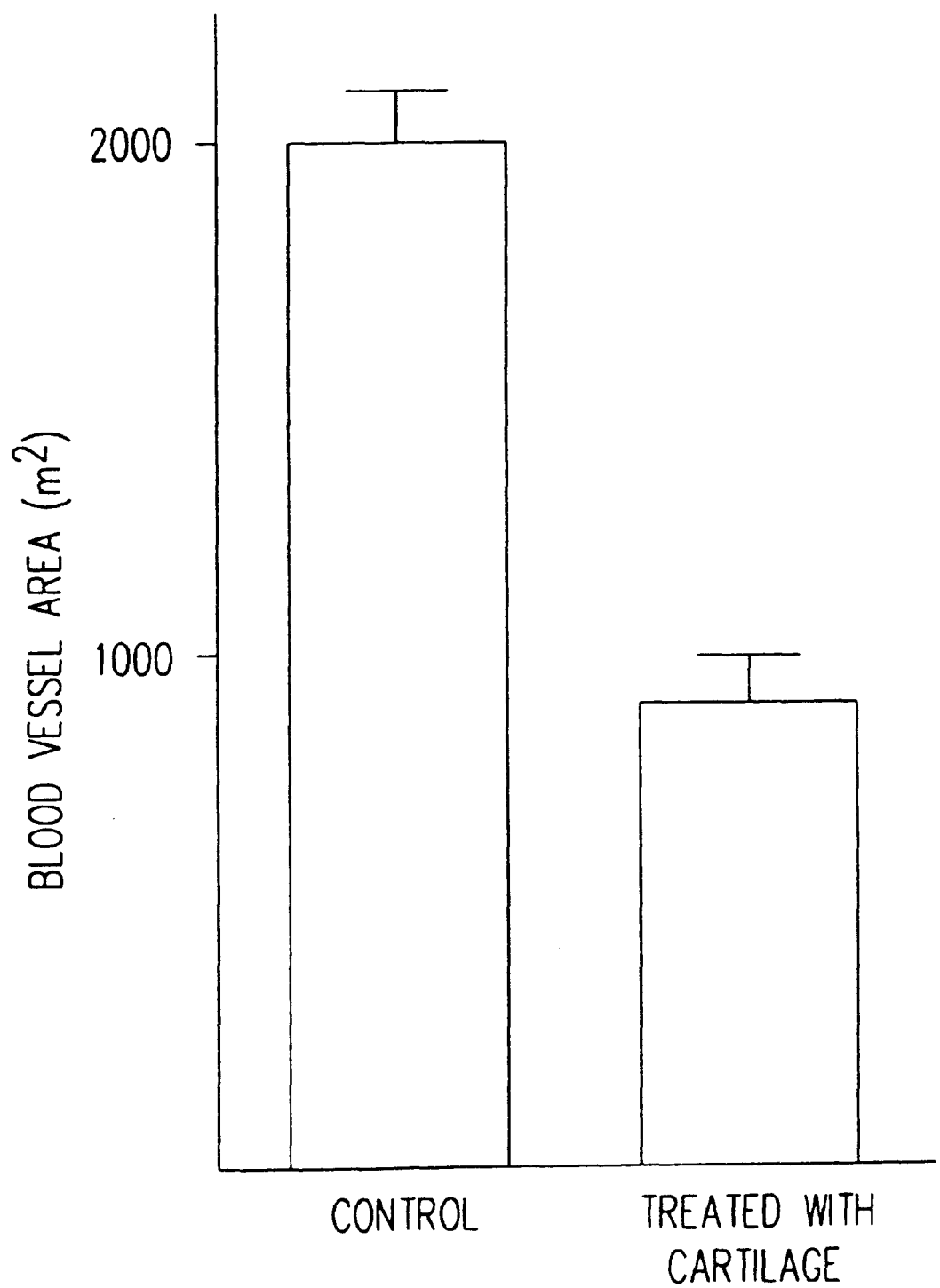
FIG. 7 is an histogram derived from FIGS. 6a) and b), illustrating the effect of cartilage extract on blood vessel area in tumors.

FIG. 7 shows that, when a combination of lyophilizate (p.o.)-supernatant (p.o.+i.p.) was used (refer to FIGS. 6a and b), a decrease of 55% of the blood vessel area was observed in the tumor.

The diminution of the tumor size might be due to an important decrease in its vascularization, to a direct effect on tumor cells, or a combination of both phenomenons. The anti-angiogenic effect of these extracts is well depicted above. The direct hypoplasiant effect has been observed in vitro on the hormono-dependent cells, which remains to be confirmed in vivo.

Because the above-mentioned results showed that the supernatant had an increased effect over and above the effect of the lyophilizate on ZR75-1 cells, the components thereof were further investigated.

OBTENTION OF LIQUID FRACTIONS CONTAINING ACTIVE MOLECULES

Shark cartilage was harvested and processed the same as described above. After centrifugation, the pellet was discarded and the supernatant was processed the same way as described above up to the sterile filtration on 0.22 μm filter.

The supernatant will be hereinbelow referred to a crude permeate, e.g. the product after the ultrafiltration.

The so obtained crude permeate was passed on FPLC (Fast Protein Liquid Chromatography).

FPLC conditions

Column: Hiload 26 mm ×60 cm SEPHACRYL S-300™ (cross-linked co-polymer of allyl dextran and N,N methylene bisacrylamide FPLC system: from Pharmacia All samples were filtered on 0.22 μm filter before loading on the column. The elution buffer was phosphate buffer saline (PBS) filtered and degazed during 15 minutes. The volume of the loaded sample was usually 3.2 mL (could be up to 13 mL). The flow rate was 1 mL/minute. Fractions of 10 mL were collected. The eluted compounds were detected by their U.V. absorbance (280 nm). A calibration chart was obtained by using the MW-GF-1000 calibration kit from Sigma, this calibration sample having the same volume as the loaded sample to analyse (3.2 mL). The elution volume of a sample was deduced from the plotting of the molecular weight of the compounds of the calibration kit versus their elution volume to which was subtracted the void volume of the column. The void volume was obtained by injecting dextran blue (M.W.=2,000,000). The fractions were tested on ZR75-1 cells for their activity. The fractions of interest were identified and their characteristics were corroborated by further study (hereinbelow).

Additional characterization of the active components of the permeate was conducted on Rotofor (Biorad 170–2950; see isoelectrofocalization below) and on Amicon filters of different cut-off values to obtain fractions of molecular weight of between 10–30 KD, 30–100 KD and more than 100 KD.

Isoelectrofocalization

A preparation of shark cartilage (46 mL of permeate 1 Kg/L) was dialysed overnight against 4 liters of pure water containing 5% glycerin at 4° C. using a membrane Spectra pore #7 MWCO 3500 KD (Spectrum 132110). The dialyzed solution was mixed with 2.75 mL of ampholytes (Pharmacia #80-1125-87) pH 3.5–10.0 and 0.5 g CHAPS (Sigma C3023; 3-[(3-Cholamidopropyl)-dimethylammonio]-1-propane-sulfonate). The volume was completed to 55 mL with pure water. The solution was loaded on Rotofor. Isoelectrofocalization was conducted at 4° C., at a constant power of 12 watts (3000 xi power supply Biorad 165–0554), under constant water circulation for insuring maintenance of the temperature. At the beginning of the separation, the voltage was 380 volts and the amperage 31 mA. When the amperage was stabilized (at 14 mA), the voltage read 870 volts. The isoelectrofocalization was stopped and 20 fractions were collected.

| FRACTION | VOLUME (mL) | pH |
|---|---|---|
| 1 | 3.7 | 3.56 |
| 2 | 2.1 | 4.01 |
| 3 | 2.2 | 4.18 |
| 4 | 2.3 | 4.31 |
| 5 | 2.2 | 4.63 |
| 6 | 2.1 | 5.03 |
| 7 | 2.5 | 5.30 |
| 8 | 2.1 | 5.50 |
| 9 | 2.4 | 5.81 |

-continued

| FRACTION | VOLUME (mL) | pH |
|---|---|---|
| 10 | 2.5 | 6.26 |
| 11 | 2.3 | 7.00 |
| 12 | 2.4 | 7.29 |
| 13 | 2.4 | 7.64 |
| 14 | 2.5 | 7.94 |
| 15 | 2.3 | 8.32 |
| 16 | 2.5 | 8.62 |
| 17 | 2.4 | 8.94 |
| 18 | 2.9 | 9.30 |
| 19 | 3.1 | 9.88 |
| 20 | 3.6 | 10.71 |

The identification of these proteins was made by estimating their molecular weight on an electrophoresis gel (Laemmli, U.K. (1970) Nature (Lond.) 227: 680).

Figure 8A:
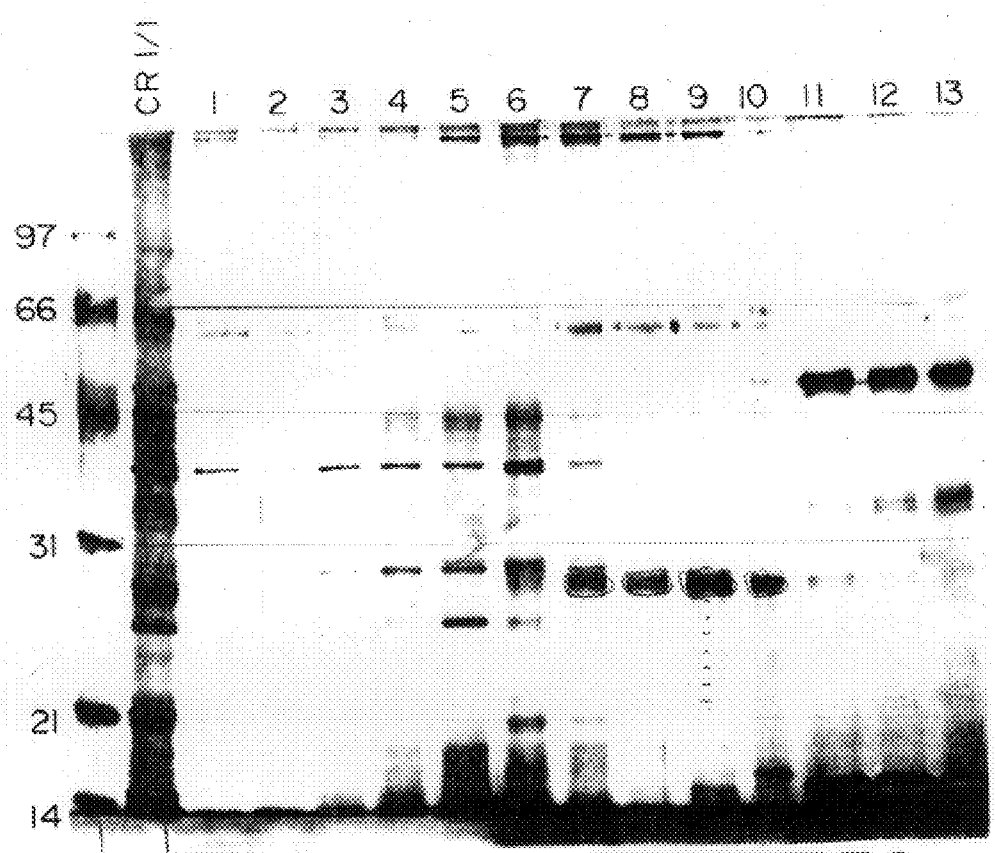
FIG. 8 represents the electrophoretic profile in non-denaturing conditions of liquid fractions separated on Rotofor; molecular weight markers appear at the left followed by a sample of the crude permeate before fractionation, for comparison with the isolated fractions.
Figure 8B:
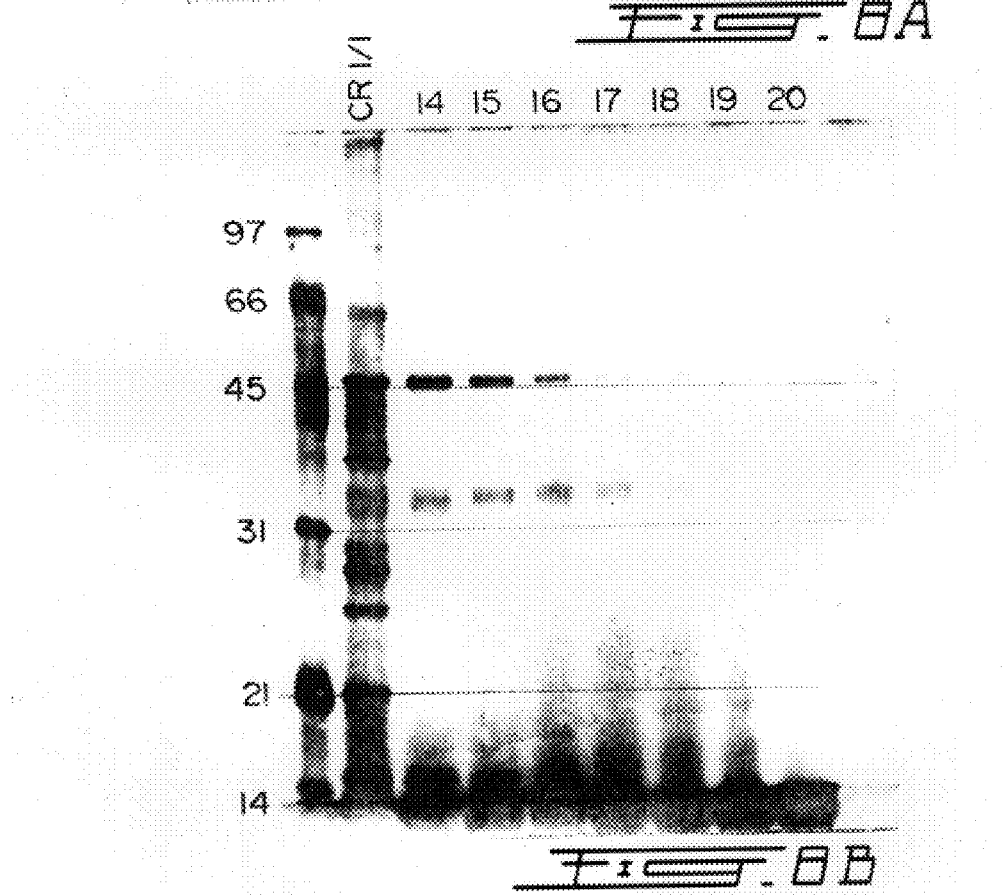

These fractions were four-fold diluted with a loading buffer (see Laemmli) and 8μL aliquots were submitted to electrophoresis in non-reducing conditions. FIG. 8 shows the electrophoretic profile of each fraction and of the material before isoelectrofocalization.

All the fractions were sterile-bottled under a laminar flow hood by passing them through a sterile Millipack-60 filter having a porosity of 0.22 μm.

The protein content of the fractions was evaluated by the Lowry dosage method. Solutions of 1 Kg/2 L (expressed as the crude cartilage weight per litre of permeate) were tested on ZR75-1 cells at different concentrations in culture medium. The results are summarized as follows:

$1^{st}$ test

The permeate was lyophilized, resuspended in PBS, and run on FPLC. No hypoplasiant activity was detectable (data not shown).

$2^{nd}$ test

Tests performed on Rotofor fractions (The permeate was concentrated by evaporation): Protein identification

| Fractions Identified | Isoelectric Point | Median Value | Molecular Weight |
|---|---|---|---|
| 7–8–9–10 | 5.30 to 6.26 | 5.78 | 29 ± 1 KD |
| 7–8–9 | 5.30 to 6.26 | 5.68 | 60 ± 1 KD |
| 12–13–14 | 7.29 to 7.94 | 7.62 | 48 ± 1 KD |
| 13–14 | 7.64 to 7.94 | 7.79 | 35 ± 1 KD |

$3^{rd}$ Test performed on FPLC fractions (The permeate was concentrated by evaporation):

| Fractions | Molecular Weight |
|---|---|
| 6 and 7 | 1 – 2.5 KD |

$4^{th}$ test performed on 100 μL fractions obtained on Amicon molecular filters:

| Concentration tested | Molecular Weight | Inhibition of ZR75-1 Cell Cultures |
|---|---|---|
| 100 μg/mL | MW > 100 KD | 64% |
| 100 μg/mL | 30 KD < MW < 100 KD | 114% |
| 100 μg/mL | 10 KD < MW < 30 KD | 127% |
| 400 μg/mL | MW < 10 KD | 149% |

FPLC fractions 6 and 7 contain active components of a very small molecular weight: 1 to 2.5 KD.

The hypoplasiant effect of the fractions can be up to 33 000 times higher than the one observed with the lyophilizate.

The above results show that lyophilization appears to provoke some loss of the direct anti-tumoral activity of the proteins contained in the eluate while no such abolition occurred with the lyophilization of the solid extract. This suggest that the active components included in cartilage particles appear to be in an environment such that they are less sensitive to the denaturing effect of the lyophilization. Since the hypoplasiant activity is sensitive to lyophilization, when retrieved in water, it is probable that the addition of stabilizers or protective agents to the total extract or to a particular fraction containing this activity prior to lyophilization would substantially preserve the activity.

Further identification of the active components of the eluate

The active fractions (tested on ZR75-1 cells) are retrieved in the following range of molecular weights, determined by another type of purification starting with the same permeate (1 Kg/L) on a 10 mm diameter×30 cm length Superose-12 column using the FPLC and rotofor procedures described above. A flow rate of 1 mL/minute was selected. 45 fractions of 1 mL were collected.

| Fractions 20–21 | activity in fractions corresponding to a molecular weight of 70 to 120 KD |
| --- | --- |
| Fraction 22 | activity in fractions corresponding to a molecular weight of 60 to 70 KD |
| Fractions 29–32 | activity in overlapping fractions corresponding to a molecular weight of 35 to 46 KD |
| Fractions 34–35 | activity in fractions corresponding to a molecular weight of 29 KD |
| Fractions 38–39 | activity corresponding to a molecular weight of 1 to 2.5 KD |

SPECIFICITY

In order to evaluate the specificity of activity on tumor cells, the permeate obtained after ultrafiltration was tested on other mesenchyme originating cells, human TENON fibroblasts (HTFs), which are normal fibroblasts.

B. In Vitro a. Patients

Only the HTFs from two patients (one with neovascular glaucoma, NVG, and the other with primary open angle glaucoma, POAG have been used.

b. Subculturing and Maintenance of HTFs

Each confluent culture were passaged by washing and detaching with 0.5 ml of 0.05% trypsin/0.5 mM EDTA (Gibco 610-5300 AG) for 5–10 minutes at 37° C. 1.5 mL of DME/F-12 medium containing 15% fetal bovine serum (FBS) was then added to neutralize trypsin/EDTA.

Association of the cells was made by triturating and transferring into 25 cm² T-flasks, into which additional medium containing 10%(FBS) was added. After confluence was reached, the HTFs were transferred into 75 cm² and eventually, into 180 ²cm T-flasks. When enough cells were obtained, some cells were utilized for the experiments as described below, and others were simultaneously frozen to preserve identical passages for future experiments.

c. Experimental Protocols

When confluence was reached, cells from one patient growing in two or three identical 180 cm² T-flasks were dissociated by the procedure described above. After a short low speed centrifugation, they were counted with a ZMI Coulter Counter 216013, equipped with a 256-Channelyzer.

For all of the in vitro experiments which follow, approximately fifty thousand cells were inoculated in 1 mL of DME/F-12 medium containing 1% FBS into each 16 mm dish and a 12-well plate. Seventeen hours (hrs) after seeding, 1 mL of fresh identical medium supplemented with 1% FBS ("absolute" controls) was added. Depending on the experimental design (see above and below), the 1% FBS medium was supplemented or not with GFs (Growth Factors) or with the permeate 1 Kg/2L (cartilage weight/water volume) solution and sterile filtered. On this day (day 0), some samples of cells were also counted to determine plating efficiency (which should be equal or greater than 95%).

Forty-eight hours after the onset of the experiments, the cells were rinsed and dissociated by the afore-mentioned procedure and counted again. The number of cells was expressed as a percentage of that obtained in the "absolute" controls.

Each "absolute" or positive control, containing 1% or 5% FBS, respectively, and each experimental group, supplemented with 1% FBS and with an individual GF or cartilage permeate consisted of triplicate samples.

Each experiment was carried out on the cells of one or two patients at a time, and was repeated at least twice.

Stimulation of fibroblast proliferation by growth factors (GFs) or cartilage permeate was compared to the stimulation of the same by 5% FBS.

In these experiments, GFs, porcine platelet-derived growth factor (pPDGF) and human recombinant basic fibroblast growth factor (hr bFGF) (gift to Dr. P. Brazeau from Farmitalia Carlo Erba, Milan, Italy) were added in concentrations of 10 to 100 ng/mL in 1% FBS, respectively. Forty-eight hours after the onset of the experiment, the cells were dispersed by Trypsin-EDTA and counted on the Coulter counter. All triplicate values (columns 1,2 and 3) appearing below equal one twentieth of counts per well.

Patient B: Glaucoma    Sexe: Male    Age: 53
HTF
Day −1: number of cells per well: 46170
        DME/F12 - 1% FBS - 1% Pen. Strep
Day 0:  number of cells per well: 65214
        DME/F12 - 1% FBS - 1% Pen. Strep
Day 1:  number of cells per well: 62548
        DME/F12 - 1% FBS - 1% Pen. Strep
Day 2:  number of cells per well:
        DME/F12 - 1% FBS - 1% Pen. Strep

| | | Sample/plate | | | | nb cell/count | % control |
| --- | --- | --- | --- | --- | --- | --- | --- |
| | | DME/F12 | 1 | 2 | 3 | AVE. | SEM | growth |
| Plate #1 FBS | 1 | Day 0 1% FBS | 3,0 19 | 2,8 62 | 2,8 53 | 65,214 | 71 | |
| | 2 | Day +1 1% FBS | 2,7 11 | 2,9 73 | 2,6 93 | 62,548 | 1,655 | |
| | 3 | Day +2 1% FBS | 2,2 84 | 2,4 00 | 2,1 91 | 51,333 | 1,655 | 100 |
| | 4 | Day +2 5% FBS | 3,0 84 | 2,8 34 | 3,1 15 | 67,446 | 1,627 | 131 ** |
| Plate #2 PDGF | 5 | DME/F12 Control (1% FBS) | 2,5 58 | 2,1 81 | 2,2 16 | 51,931 | 2,19 9 | 100 |
| | 6 | 1 ng/ml 1% FBS | 2,4 25 | 2,5 80 | | 56,056 | 1,228 | 108 |
| | 7 | 10 ng/ml 1% FBS | 4,0 80 | 3,9 75 | 4,2 82 | 92,116 | 1,648 | 177 *** |
| | 8 | 100 ng/ml 1% FBS | 4,6 25 | 4,3 56 | 4,4 50 | 100,285 | 1,442 | 193 *** |
| Plate #3 b-FGF | 9 | DME/F12 Control (1% FBS) | 2,91 5 | 2,5 33 | 2,5 02 | 59,360 | 2,429 | 100 |
| | 10 | 1 ng/ml 1% FBS | 2,74 4 | 2,5 54 | 2,7 61 | 60,174 | 1,213 | 101 |
| | 11 | 10 ng/ml 1% FBS | 3,60 6 | 3,1 43 | 3,1 93 | 74,234 | 2,683 | 125 |
| | 12 | 100 | 4,06 | 3,0 | 3,0 | 75,585 | 6,307 | 127 |

-continued

| | | | ng/ml<br>1% FBS | 4 | 33 | 26 | | | |
|---|---|---|---|---|---|---|---|---|---|
| Plate #4<br>CARTI-<br>LAGE<br>(1 Kg/2L)<br>(filtered) | 13 | | DME/F12<br>Control<br>(1%<br>FBS) | 2,826 | 2,566 | 2,486 | 58,822 | 1,877 | 100 |
| | 14 | | 1 µl/ml<br>1% FBS | 2,729 | 2,576 | 2,575 | 58,837 | 936 | 100 |
| | 15 | | 10 µl/ml<br>1% FBS | 2,643 | 2,493 | 2,584 | 57,643 | 798 | 98 |
| | 16 | | 100 µl/ml<br>1% FBS | 2,918 | 2,883 | 2,766 | 58,483 | 2,461 | 99 |

** P < 0.02
*** P < 0.01 Determined by Student-Fisher Test

While growth factors like PDGF and bFGF show a stimulating activity on HTFs, no effect, positive or negative, has been observed when these cells are grown in the presence of cartilage permeate (1 Kg/2 L). No hypoplasiant effect could be observed. This suggests that the permeate has an hypoplasiant or cytotoxic effect which is specific to tumor cells with no detectable effect on normal cells. The same cartilage extract neither had an effect on another type of fibroblast cells, HSF (Human Skin Fibroblasts; data not shown). Eventhough not tested, it is assumed that the lyophilizate also shows no effect on normal cells.

COMPARISON WITH PRIOR ART PRODUCTS

Since we are not the first to find a great interest in cartilage extracts, we have verified the unique character of the shark cartilage liquid extract prepared by the present process in side-by-side comparison tests with two products described or deducible from the prior art, namely products prepared by the process of Balassa (U.S. Pat. No. 4,822,607) and Oikawa et al. (op. cit.). Oikawa et al. describe a method by which two main fractions are obtained, one having molecules of molecular weights comprised between 1 and 10 KDa, the second having components heavier than 10 KDa. They assign anti-angiogenic properties only to the first fraction, the other being said devoid of any anti-angiogenic activity in CAM test. For adequate comparison of Oikawa's products, we have fractionated our total liquid extract in two corresponding fractions, and we retained the one having 1 to 10 KDa. Since Balassa describes a process for extracting a total liquid extract, we have compared our total liquid cartilage extract (1 to 500 KDa) to the product prepared by reproducing Balassa's method, replacing the calve cartilage by shark cartilage as the starting material. We assume that if Balassa and Oikawa describe an equivalent process, the patterns obtained on FPLC and HPLC should overlap substantially, and that the products when tested in CAM test should show similar activity as ours. All samples were made to a final concentration of 12 µg/µL (dry weight/volume solution) prior to FPLC and HPLC chromatography. Oikawa's product was centrifuged and filtered prior to chromatography because it contained unsoluble material.

A) FPLC conditions: Superose 12 (Pharmacia); gel permeation column.

B) HPLC conditions: CS-S-hexyl column 5 µm, 25×0.94 cm, CSC #059–085; reverse phase column.

Shark cartilage samples extracted by the three methods were labelled (with estimated dry weight per volume of solution) as follows:

1) DUP is the preparation of the present invention fractionated to contain molecules between 1 to 500 kDa (12 µg/µl);

2) BAL is the preparation according to the recipe of Balassa et al. (12 µg/µl);

3) OIK is the preparation of fraction 3 according to Oikawa et al. (270 µg/µl). All samples were made to a final concentration of 12 µg/µl (dry weight/volume) prior to any analysis. The OIK sample had a high amount of insoluble material which could be pelleted readily by centrifuging at 13,200 RPM or filtering through a 0.2 µm membrane. Filtration or concentration of insoluble material was essential prior to FPLC and HPLC (A, B).

A) FPLC Results Summary

Samples were run on a SUPEROSE S-12™ (cross-linked agarose) (10/30) gel permeation column with phosphate buffered saline (PBS) as eluent at a flow rate of 0.5 ml/min (chart speed=0.25 cm/min). A 100 µl aliquot of the concentration adjusted samples were filtered through a 0.2 µm membrane before injection. OD280 was monitored.

The column was calibrated with the following standards (MW in daltons): catalase (232,000), aldolase (158,000), albumin (56,000), ovalbumin (44,000), chymotrypsin (25,700), ribonuclease (13,700), insulin (5,700), insulin B chain (3500), insulin A chain (2500) bacitracin (1450), vitamin B-12 (1355). Molecular weights of the major peaks were calculated by the following equation: $Log_{10}$ MW=7.52–0.212×RT, where RT =elution volume in mL. $R^2$=0.976. Total column volume ($V_T$) was 21.93 mL as determined using cytidine (246 Da). Void volume ($V_0$) was determined to be 8.38 mL with blue dextran ($2 \times 10^6$ Da).

In FIG. 10a), our sample DUP had a first major peak (1) which eluted at 18.76 mL giving a molecular weight of 3500 Da. Subsequent peaks at 22.7 (2) and 27.3 mL (3) were beyond the total column volume (21.93 mL, as determined by cytidine). These peaks appear to have some affinity for the column matrix.

In FIG. 10b), Balassa's sample BAL had a small peak (1) eluting near the $V_0$ of the column (8.4 a mL), a peak (2) at 18.5 mL (4000 Da) and two peaks eluting after the $V_T$, (3) 22.6 min and (4) 28.2 mL.

In Figure 10c, Oikawa's sample OIK also had a small peak (1) at the $V_0$, peak (2) at 18.9 mL (3300 Da), peak (3) at 21.5 mL (1000 Da) and small peak (4) at 27.3 mL.

In comparing the samples, it is notable that aside from the 3300 Da peak, that the major bands of the DUP sample were not observed at the same intensity in the other samples. The OIK sample did appear to have a small amount of the 27.3 mL peak. The BAL sample had a peak migrating at 28.2 mL which could correlate with one the minor peaks in the DUP sample.

B) HPLC Results Summary

For HPLC on a hexyl-reverse phase column, OD210 and OD280 were monitored simultaneously. 50 µl aliquots of centrifuged samples (all at 12 µg/µl) were loaded and eluted with 100% $H_2O$. Peaks for each chromatogram labelled according to OD210 (eg. 1) and corresponding OD280 peaks are noted by '(eg. 1)'. The $V_0$ of this column was 5.5 mL (1.4 min).

Figures 11A, 11B, 11C:
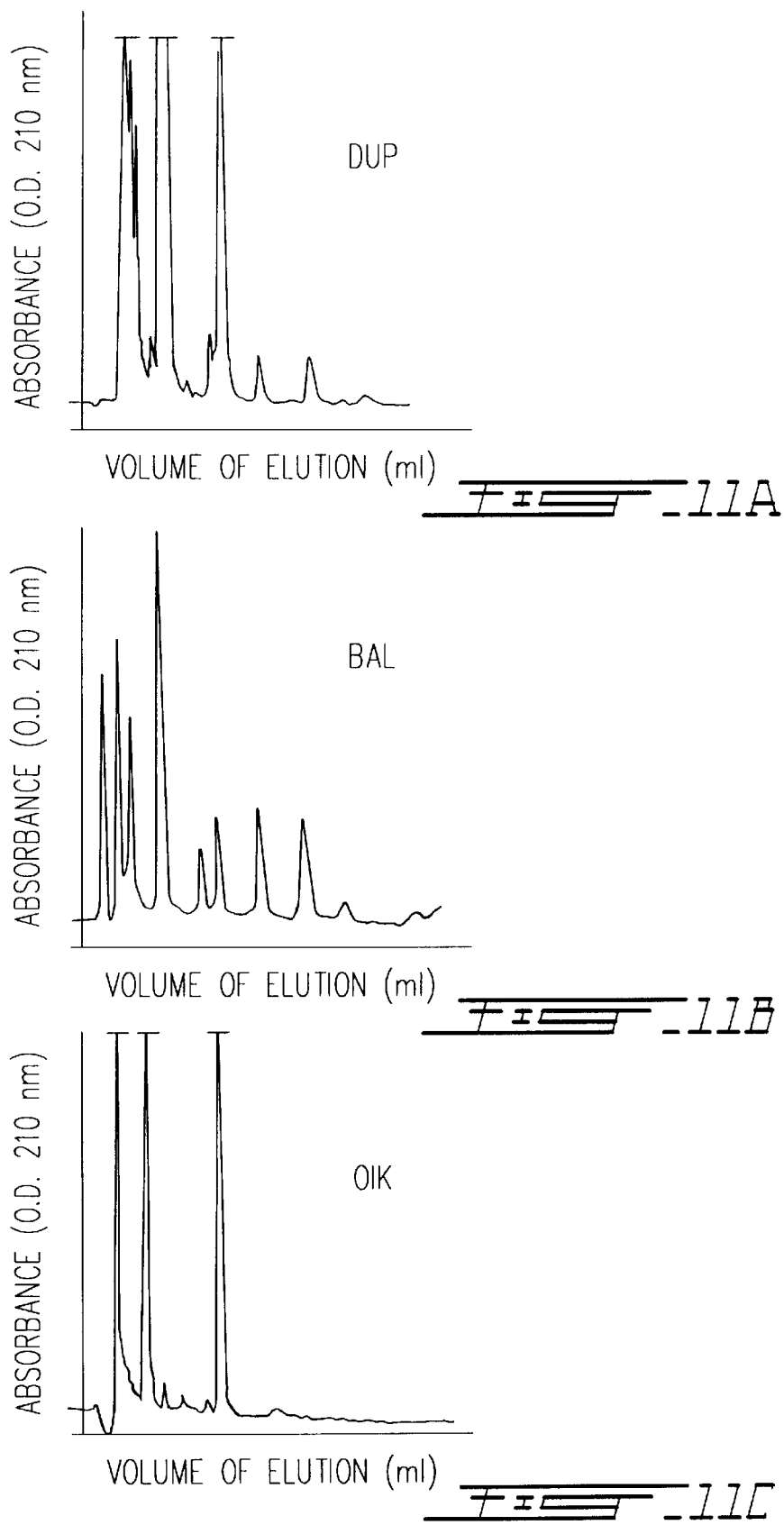
FIGS. 11a), 11b) and 11c) show a HPLC migration pattern of the same extracts defined in FIGS. 10a), 10b) and 10c).

In FIG. 11a), DUP had 3 major peaks which were observed via OD210 (1,2,3) and 2 minor peaks (4,5). Two side peaks were observed off of peak 1, labelled 1a and 1b. Significant OD280 absorbances were associated peaks 1, 1a, 1b and 3. In comparison, the corresponding OD280 absorption for peak 2 is much smaller relative to the OD210.

In FIG. 11b) BAL showed more OD210 peaks, but the intensities were lower relative to the DUP peaks. As far as overlap of peaks could give an indication of identity of molecules, only peaks 3 and 7 in the Balassa sample appear to correlate with the retention times of peaks in the DUP sample (peak 1a or 1b and peak 4, respectively).

In FIG. 11c), only three major peaks were observed (1,2,3) in OIK extract. Peaks 1 and 3 could correlate to peaks 1 and 3 of DUP sample but no side peaks of 1 were observed in the OIK chromatogram. The height of the peaks in the OIK sample were lower than the DUP. Even though the FPLC and HPLC patterns are characteristic of distinguished products, we have verified the anti-angiogenic activities of the three products in CAM tests.

CAM Test

Figure 12:
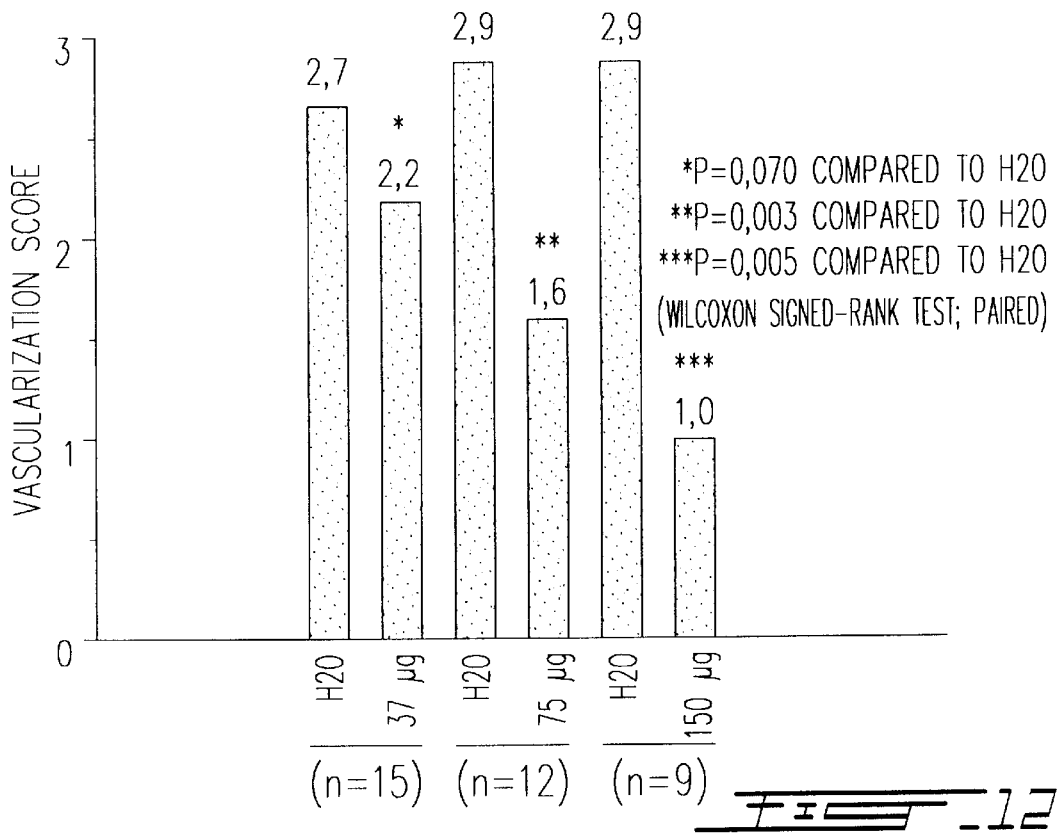
FIG. 12 shows the results of CAM-tests performed using different concentrations of protamine, an anti-angiogenic reference compound, when compared to control.

CAM tests were first performed using different concentrations of protamine (37, 75 and 150 $\mu$g). A methylcellulose disk containing water and another disk containing protamine, as positive control, were placed on the chorloallantoic membrane of a chick embryo (n=number of embryos analysed). An O-ring was placed on each disk to ease their localization. The next day, the level of vascularization in each O-ring was scored by a pair of scientists in the usual blind fashion. Evaluation scale for the CAM-test based on the 1-2-3 score: (score=3) Normal vascularisation when compared to the opposite horizontal quadrant or the matching quadrant of a control embryo; (score=2) Blood vessels enter the O-ring but vanish at mid-course. Major blood vessels cross the O-ring but their trajectory is clearly affected. Decreased branching, decreased vascular area of the quadrant in the vicinity of the O-ring; (score 1) No blood vessels or deviated blood vessels within the O-ring. Blood vessels do not grow beyond the O-ring except if they bypass the latter and go beyond it. Vascular area of the quadrant clearly diminished in the vicinity of the O-ring. In FIG. 12, the values above each column show the final score for each sample. Wilcoxon statistical test was used to compare the significance of the differences between the two disks placed on the same egg. A dose-response relationship is observed as expected.

Figure 13:
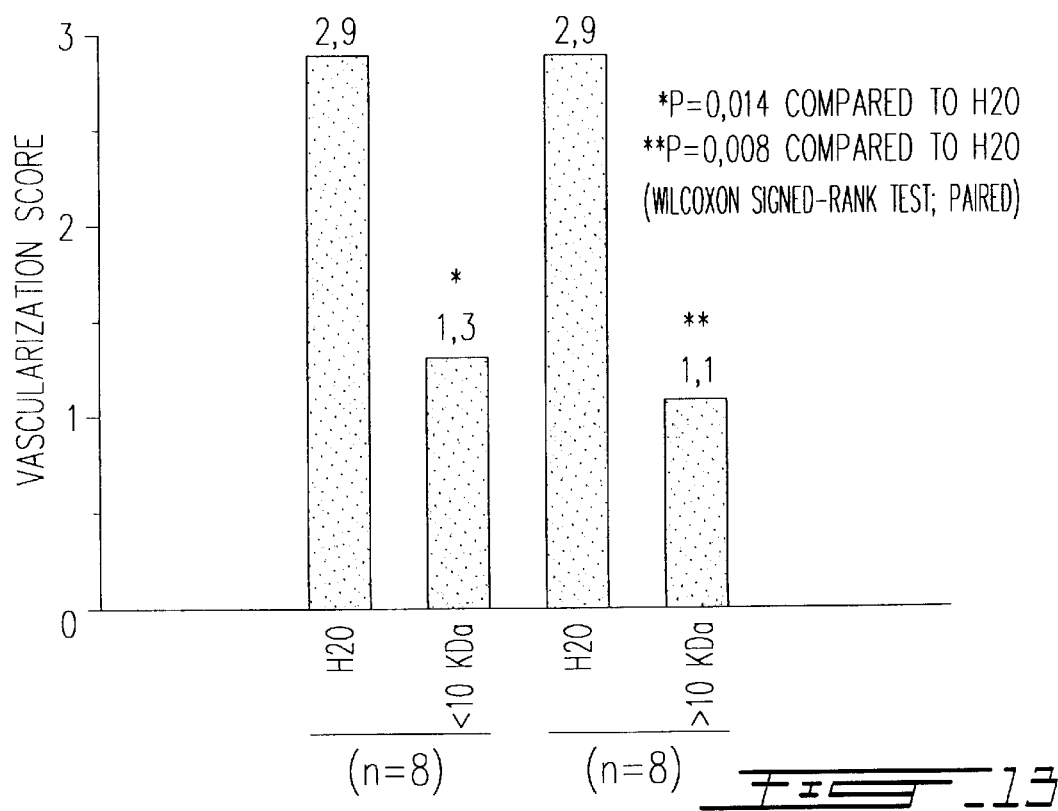
FIG. 13 shows the results of CAM-tests performed with two fractions of the present total liquid extract of shark cartilage of our invention (DUP), one having molecular weight lower than 10,000 Daltons, the other one having molecules higher than 10,000 Daltons.

The lower and higher than 10 KDa fractions of DUP extract were tested in the same conditions. They were shown equally potent (FIG. 13) in inhibiting neovascularization.

Figure 14:
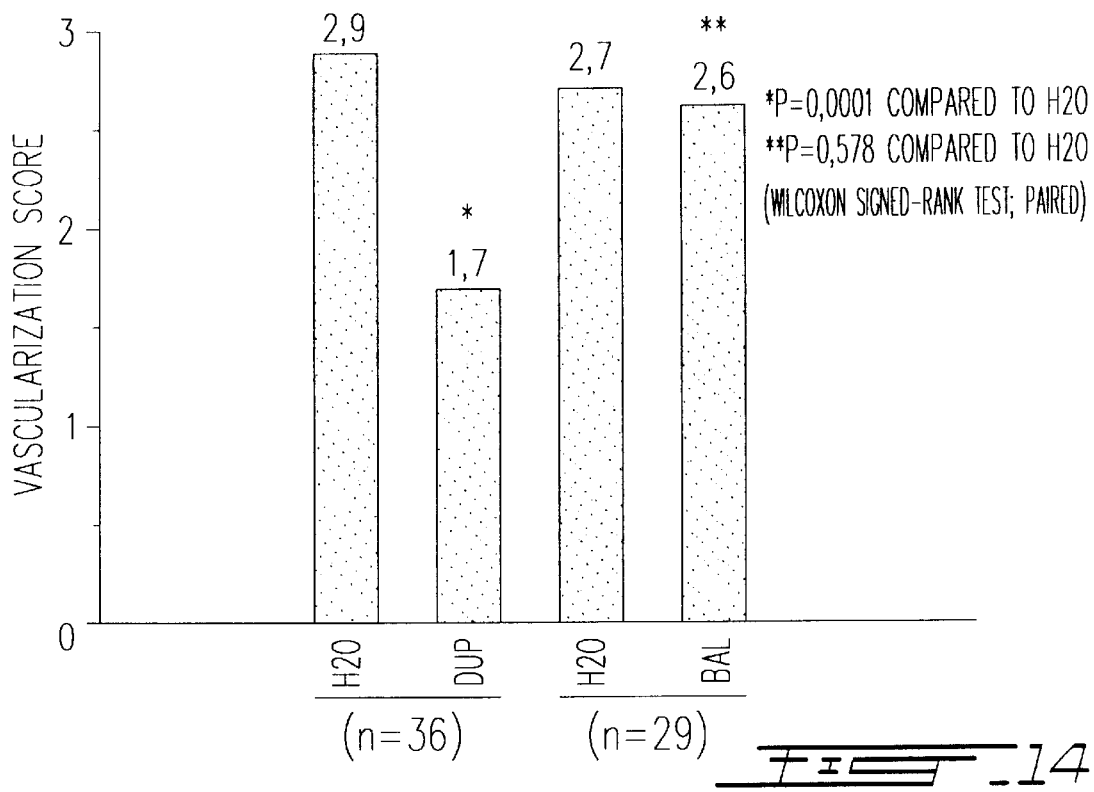
FIG. 14 shows the results of CAM-tests performed with the total liquid extract of our invention (DUP) when compared to an equivalent concentration of a product made by the process of Balassa (BAL).

Our total extract DUP was compared to the product prepared by Balassa's process BAL. No significant anti-angiogenic activity was retrieved in Balassa's product (FIG. 14).

The DUP crude extract was compared to the fraction 3 in Oikawa OIK. Both DUP and OIK were almost equivalent (FIG. 15). Oikawa et al. nevertheless taught away from the present invention since they mentioned that no activity was detectable in the fraction of molecular weight higher than 10 KDa, which is in contradiction with our results of FIG. 13.

Therefore, despite similarities between Balassa's and our processes, the products obtained by both processes are clearly not the same.

The two prior art products that have been compared to ours are yet considered as classical processes to prepare cartilage extracts. The above results show that the present process provides products of unexpectedly good activity, as far as anti-angiogenic activity is concerned. Since other activities will be hereinbelow verified, we can assume that the present process has indeed succeeded in recovering a multiplicity of hydrosoluble activities in one single extract.

CLINICAL TRIALS

Before proceeding with preliminary clinical trials, the crude permeate obtained after ultrafiltration was 2 and 20 fold-concentrated, providing enriched active permeate. These levels of concentration were obtained on a tangential flow filtration column having a porosity of 1000 Daltons, which reduced the volume of the eluate by 2 and 20 times. The concentrated permeate was filtered of a millipore filter of a porosity of 0.22 $\mu$m. When the cartilage was processed with the alternative centrifuge method (using the CEPA centrifuge with a membrane of a porosity of 30 $\mu$M), a ten-fold concentration achieved the obtention of a concentrated extract having almost the same proteic level as the above 20-fold concentrated extract, e.g. about 12–25 mg/mL (improved method) instead of about 8–12 mg/mL (laboratory scale method). The sterile 10× concentrated permeate was distributed in 7 mL aliquotes (about 85 mg of proteins) in sterile flasks, frozen at −80° C. overnight and further stored at −20° C. until utilization. The major difference between the crude and the concentrated permeates is their concentration in proteins. It will be noted that the method used for determining the proteic content measures the total nitrogen compounds and not only proteins (Kjeldahl method). This may explain why the concentration of proteins does not increase proportionally with the level of volume concentration as this is usually the case when the proteic content is determined by the Lowry method. The concentration step is thus assumed to allow permeation of water as well as low molecular weight nitrogen compounds.

ANTI-ANGIOGENIC EFFECT

The concentrated permeate was used for treating angiogenesis-dependent diseases. Three different types representative of angiogenesis-dependent diseases were tested in the practice in human; the first type being cancer (prostate cancer), the second type being dermatological disorders (psoriasis), and the third type being arthritis. The examples below will illustrate and indicate at least the antiangiogenic activity of the liquid extract.

Among dermatological diseases, psoriasis cases were selected. Among the psoriasis cases tested, it is worthwhile noting a difference between psoriasis cases complicated by hyperkeratosis and non-complicated ones. The keratosis component is the formation of cornified envelope in the form of a plaque. Such a plaque is a physical barrier which impedes the efficient penetration of the active ingredients towards the blood vessels.

A patient suffering of a prostate cancer has voluntary tried a 10 fold-concentrated cartilage permeate. This patient underwent a series of successive conventional therapies that were temporarily successful. He recently began to consume the cartilage extract after his cancer showed recidivism.

Other volunteers suffering of arthritis and having previously taken medication (prednisone) or not started consuming a concentrated cartilage extract. Their condition improved as verified by the reduction of pain and stiffness in the joints.

The results shown hereinbelow are very encouraging and are deemed predictive of the usefulness of the crude permeate and fractions thereof in the treatment of all angiogenesis-dependent diseases, and not only to the ones specifically tested. Insofar as a disease has an angiogenic component, it is deemed that the cartilage extract of the present invention will be effective in this respect provided that it enters a composition containing an effective amount thereof and that this composition is in a suitable form for proper administration. Therefore, it will be appreciated that the present invention is not limited to the following specific compositions for use in the treatment of angiogenic diseases, since the person skilled in the art would be able to derive numerous compositions wherein choice is guided by the mode of administration thereof and the targeted ill tissue. Compositions may be administered by different routes e.g. topical, oral, sublingual, rectal, intravenous, intramuscular, by diffusion, etc.

Because of the fishy taste and smell of the cartilage extract, flavoring agents or fragrances may be added to these compositions to encourage patient's compliancy.

PSORIASIS

The following dermatological composition was made and tried to verify its efficacy in patients suffering of psoriasis:

EMULGADE™ CLB 29% (W/W)
20× crude permeate 69.5% (W/W)
GERMABEN™ II 1% (W/W), and
Lavandula Angustifolia 0.5% (W/W)

EMULGADE™ CLB, a mixture of stearate esters, fatty alcohols and nonionic emulsifiers (purchased from Henkel Canada Ltd.) was heated at 65–70° C. under agitation. Heating was stopped while the mixture was kept under agitation. When the mixture reached a temperature of 45° C., the essential oil Lavandula Augustifolia and the preservative agents GERMABEN™II (diazonidyl urea 30%, methylparaben 11%, propylparaben 3% and propylene glycol 56%; purchased from Sutton Laboratories, N.J., U.S.A.) were added. When the temperature of the mixture reached 30° C., the cartilage extract was added. The composition so obtained was a smooth non-greasy cream; by varying the percentage of EMULGADE™, other forms of various viscosity dermatological compositions can be obtained, in accordance with the manufacturer's directives (milk, lotion, ointment). Other vehicles or excipient might be used to obtain pastes, gels and any other form of transdermal preparation.

Figure 9A:
FIGS. 9a), 9b), 9c), and 9d) illustrate the significant improvement of the condition of two patients suffering of psoriasis, one with hyperkeratosis 9a) and 9b), and the other one without hyperkeratosis 9b), 9c) and 9d), when treated with a topical composition containing an effective amount of concentrated liquid cartilage extract (lower photographs) compared with their initial condition (upper photographs).
Figure 9B:
Figure 9C:
Figure 9D:

The above formulation was given twice daily during a period of twelve weeks to a panel of 9 patients (topical application) suffering of psoriasis that had been responsive to the conventional therapies tried but became refractory to them after a while. For this study, patients were selected for the similar and symmetrical extent of psoriasis on both side members. These trials were conducted in a double-blind fashion, neither the dermatologist nor the patients knowing which affected side was treated with the composition containing the cartilage extract and which one was treated with a control-composition. Remarkable improvement was observed in five patients whose psoriasis was not complicated by hyperkeratosis; for those having hyperkeratosis, the results were moderately good. Photographs of parts of two patients' bodies are shown in FIGS. 9a) to 9d). In FIGS. 9a) and 9b), it is demonstrated that a patient affected by psoriasis with hyperkeratosis has nevertheless shown a very significant reduction of the erythema, associated with no prurit, after only one month of treatment. The hyperkeratosis remained, however, important. Photographs of the second patient suffering of psoriasis not complicated with hyperkeratosis (FIGS. 9c) and 9d) show a much better improvement after a three month-treatment. Since psoriasis appears to be a multifactorial disease, it is assumed that the response of the patients depends on the importance of the involvement of components like angiogenesis and inflammation in the establishment and in the perpetuation of this condition. The anti-angiogenic activity is indeed present in our extract, as shown in DMBA-treated rats and CAM-tests. The anti-inflammatory activity has also been verified (discussion below). It is probable that better results might be obtained if this kind of formulation is complemented with other therapeutic agents addressing to other factors involved (keratolytic agents, additional anti-inflammatory agents, antihistaminics, immunosuppressors, etc.).

This complementation may take the form of amending the formulation to include an effective amount of a keratolytic agent, for example. It could also be achieved by the separate administration of such a complementary therapeutic agent, concurrently or in alternation with the application of the present topical formulation. Furthermore, the complementary medication does not need to be administered by the same route.

The above formulation has shown no systemic effect (the effect being limited to the treated areas) and no secondary effect despite the high proportions in cartilage extract.

CANCER

One patient suffering of prostate cancer has tried the 10 fold-concentrated permeate. An adenocarcinoma was diagnosed in 1986. At that time, radiotherapy was undertaken. In 1991, the PSA (Prostatic serum antigen) level was 138 µg/L, when the normal acceptable higher limit is 4 µg/L. The patient then underwent a completely different therapy by castration combined with anti-androgen therapy (EUFLEX™). This treatment was efficient during three years, after which PSA level began to rise again. Since June 1994, this patient consumes the 10× permeate (daily sublingual dose of about 75 mg of proteins/7 mL of extract, equivalent to about 1–1.5 mg/kg of body weight/day). Even though a significant amount of this dose is swallowed, it is probably absorbed in the gastro-intestinal tract in substantial proportions, if one rely upon the results obtained in DMBA-treated animals (see above). The PSA levels decreased gradually from 12 to 0.9 µg/L, e.g. well within the normal level of PSA, (last results obtained in May 1995). This dose regimen can also be modified at will in accordance with the route of administration, the bioavailability of the active ingredients and the desired aggressiveness with which the pathology is to be controlled. At this time, the non-toxicity has been verified in rats (see above-examples) and in humans (data not shown).

In the other in vivo experiment performed on DMBA-treated rats, the dosage rate of the liquid extract was about 190–220 mg of proteins/Kg of body weight, which presumably had a great contribution to the reduction of the area of cancer blood vessels (55% when combined with a much larger protein quantities of lyophilizate). It is therefore assumed that a dose of about 0.1 to about 200 mg/Kg of body weight per day is an approximative reasonable range of median doses ($ED_{50}$) for treating cancer, at least partly by reducing or abolishing angiogenesis.

ARTHRITIS

Patients suffering of arthritis have tried on a voluntary basis one to two units of 7 mL total liquid extract per day for several months. These patients saw their condition improved gradually by recovery of joint function, diminution of pain and inflammation (up to about 60%). Since arthritis has angiogenic and inflammatory components, the above effect can be attributed to anti-angiogenic and anti-inflammatory activities of the cartilage extract.

NON-ANTI-ANGIOGENIC EFFECT ACNE

Even though acne is not to the inventors' knowledge, classified as a disease or disorder having an angiogenic component, it was nevertheless tempting to test the liquid cartilage extract in patients so affected. For experimenting the cartilage extract in patients affected by acne, the following gel formulation was made:

CARBOPOL™ 1.2%
Purified water 77.2%
NaOH 0.3%
PHENOXETOL™ 0.3%
TWEEN 80™ 0.3%
2× cartilage extract 20.0%
40× Aloes extract 0.5%

The 2×cartilage extract contains 9–12 mg/mL of proteins. This formulation shows a remarkable improvement of the aspect of the skin of patients affected by more or less severe forms of acne (inflammatory acne and kystic acne; data not shown).

These results may be due to an anti-angiogenic effect (thus revealing an angiogenic component in acne), or they may be due to active ingredients that have an effect other than anti-angiogenic (an anti-inflammatory effect, for example, see discussion below).

All the results obtained in the above clinical trial show the great potential of the cartilage liquid extract in the treatment of angiogenesis-dependent and/or inflammatory diseases. The amount of cartilage extract as well as the formulation thereof may be varied at will to fulfil specific needs.

One can note that, on a proteic content basis, the topical and all other compositions may contain a wide range of doses of the cartilage extract. Among the three specific categories of cases tested, very different dosages and/or formulations have been used. For all predicted applications (from ophthalmic drops to dermatological and cancer drug formulations), it is presumed that a minimal final protein concentration of the total liquid extract could be very low (from about 0.1 mg/mL). This lower range of doses depends on the accessibility and on the permeation of the active ingredients to the site of action as well as on the efficient capture of these ingredients and the sensitivity or response of the tissue to angiogenic inhibitors. The higher limit of the final protein concentration in formulations for some applications is not currently known. The highest final concentrations tried were of about 9 mg/mL of proteins in the formulation for the psoriasis cases and about 12 mg/mL in the dose unit of 7 mL administered in the prostate cancer case.

As mentioned above, the shark cartilage liquid extract may lose some of its activities when lyophilized in aqueous solution. However, the addition of stabilizers or protective agents as known in the art prior to lyophilization may preserve sensitive activities and render possible the administration of higher doses of the cartilage extract in the dry state.

CARTILAGE EXTRACT AS AN ANTAGONIST OF PROTEIN KINASE C (PKC)-MEDIATED EVENTS

Recent publications have shown that PKC activation led normal keratinocytes to produce increased amounts of interleukin-8 (IL-8), a mediator of inflammation (Chabot-Fletcher et al. (1994) J.Invest.Dermatol. 103: 509–515). Moreover, psoriatic keratinocytes produce very high amounts of IL-8, which further encourage neovascularization in psoriatic plaques (Nickoloff et al. (1994) Am.J-.Pathol. 144: 820–828). Since the cartilage extract has been shown very promising in the treatment of psoriasis, its effect has been tested in keratinocytes which PKC is activated by triphorbol acetate (TPA), a known agonist of this cellular transduction pathway.

Figure 16:
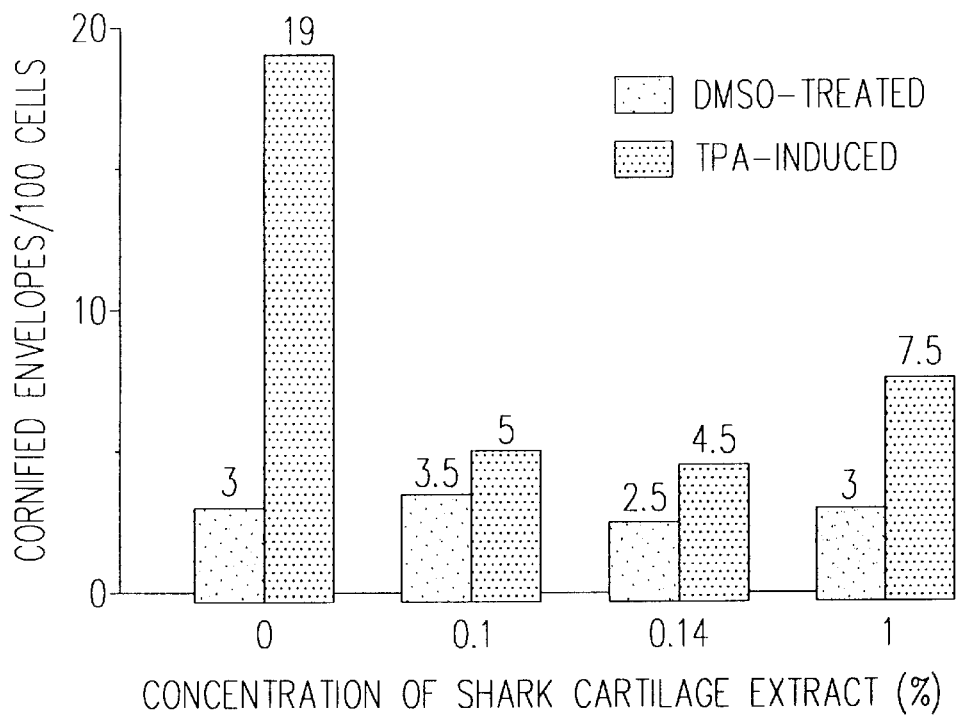
FIG. 16 shows the effect of TPA on differentiation keratinocytes when compared to a DMSO control, both measured in the presence or absence of a total shark cartilage liquid extract prepared in accordance with the present invention.

FIG. 16 shows that the level of differentiation of the keratinocytes was increased 5-fold by TPA. Shark cartilage by itself had no effect on cornified envelope formation. However, addition of the shark cartilage extract inhibited TPA-induced cornified envelope formation by more than about 60%. We do not know if TPA-induction mimics psoriatic keratinocytes. If such is the case, these results suggest that cartilage may have no effect on normal keratinocytes in vivo, while it may have an effect on psoriatic (or activated) keratinocytes. Inhibition of the production of IL-8 in TPA-activated keratinocytes as well as in psoriatic plaques or keratinocytes by the cartilage extract remains to be verified. Decreased IL-8 levels would be a valuable confirmation of the anti-inflammatory and anti-angiogenic effects of this extract.

ANTI-INFLAMMATORY ACTIVITY IS REMOTE FROM ANTI-ANGIOGENIC ACTIVITY IN SHARK CARTILAGE EXTRACT

Since angiogenesis is often associated to inflammation in numerous diseases, it would be desirable to assign each activity separately in the cartilage extract. In this regard, a skin irritation model wherein no angiogenesis is suspected to occur has been chosen to test the extract for its anti-inflammatory and soothing activity. Nine volunteers with a history of skin sensitivity to Balsam of Peru were chosen for the study. The test compounds were as follows:

1. 1× Shark cartilage 50% in D-MEM media
2. 1× Shark cartilage 20% in D-MEM media
3. 1× Shark cartilage 10% in D-MEM media
4. Cola nitida (Indena) 10% Hydro-alcohol 1:1.

Figure 17:
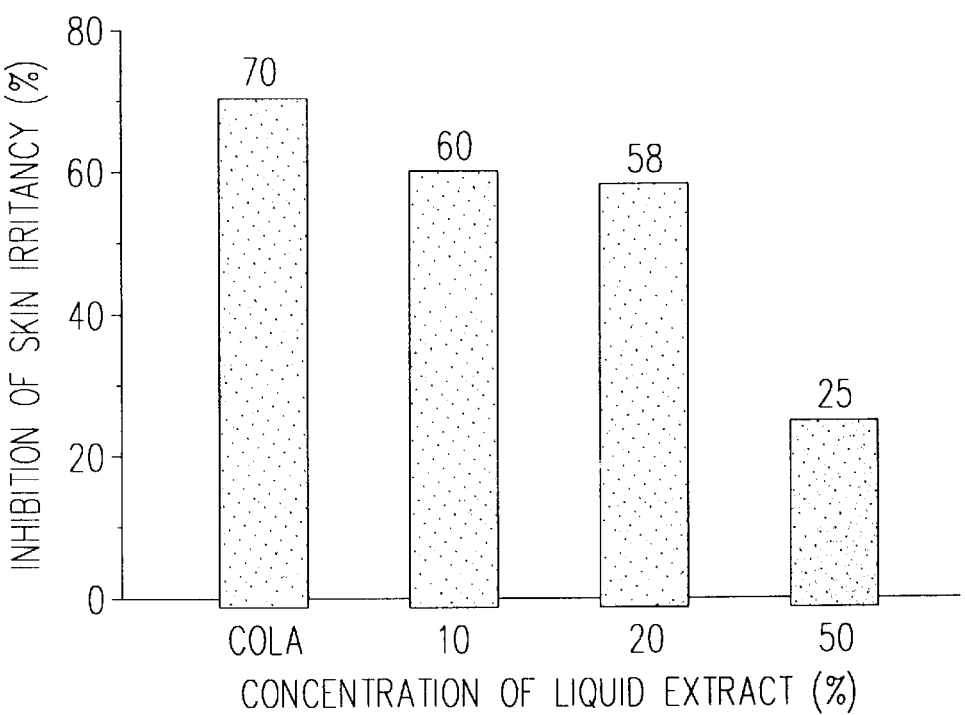
FIG. 17 shows the anti-inflammatory effect of the total liquid extract of our invention on a human model of skin irritation.

The 4 test compounds were applied on the ventral forearms of the panelists. The material was allowed to absorb for twenty minutes and then Balsam of Peru, an irritant, was applied on the test sites. Skin irritation was measured in terms of increase in skin redness. The degree of redness was measured with a Minolta Chromameter and compared with the positive and negative controls. The positive control was the color of skin treated with Balsam of Peru alone and the negative control was a skin site treated with cola solution and challenged like the test products. Statistical significance was calculated via two tailed probability T-test. FIG. 17 shows that cola at 10% was 70% active. Shark cartilage was 58% and 60% as anti-irritant at 20% and 10% concentrations, respectively. There was no dose-response effect. These results suggest that the cartilage extract contains anti-inflammatory and soothing activity which is remote from an anti-angiogenic effect.

ANTI-COLLAGENOLYTIC ACTIVITY

HPLC Chromatography

A 980 ml sample of liquid extract (DUP) was filtered through a 10 KDa cutoff membrane in a tangential flow ultrafiltration unit (PELLICON™, Millipore). The unit was rinsed first with 1 L of $H_2O$. Final yields were 480 mL of >10 KDa fraction and 1.8 L of <10 KDa fraction. The <10 KDa was concentrated by cold-finger evaporation to 180 mL (<10–10×). Eight times 100 μl aliquots of <10–10× were loaded onto CDC-S Hexyl, 5 μm HPLC column (25×0.94 cm) and eluted first with 100% $H_2O$ at 4 mL/min; then at 8.5 mL/min with 100% MeOH. Fractions were collected corresponding to $OD_{214}$ peaks.

Figure 18:
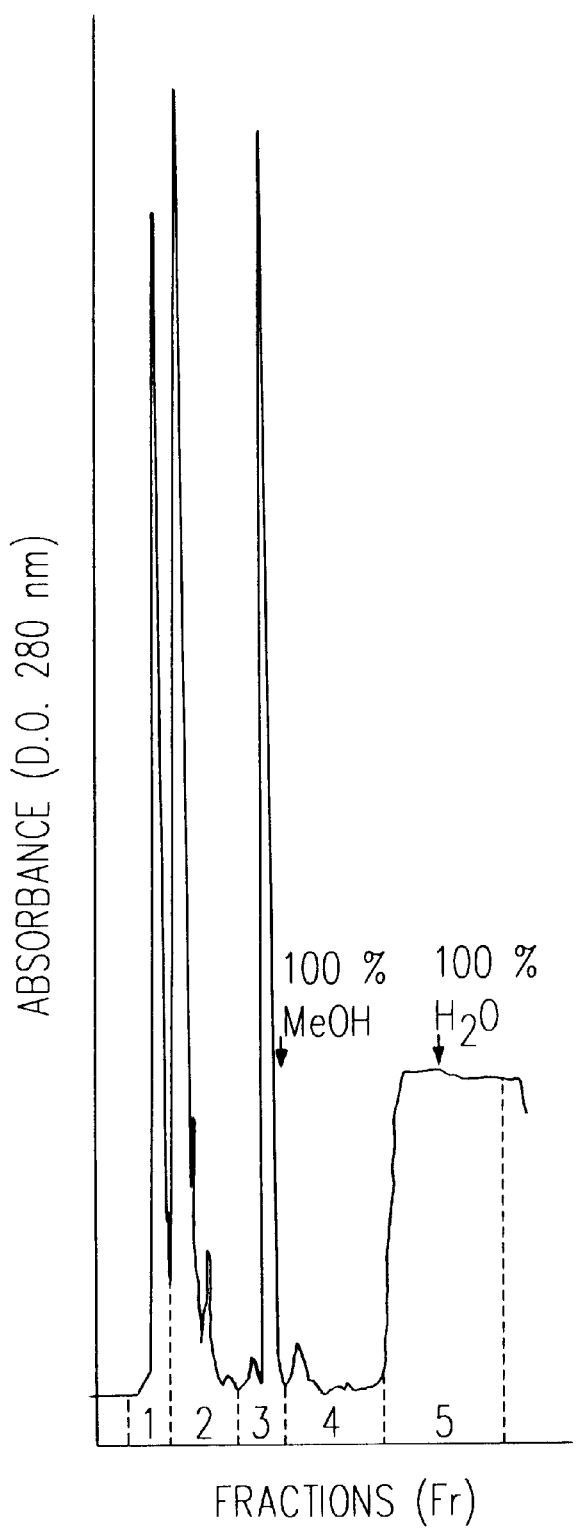
FIG. 18 shows another HPLC migration pattern of a fraction of the total liquid extract of this invention having molecular weight lower than 10,000 Daltons, which fraction has been concentrated and separated in five sub-fractions.

Five fractions were collected (FIG. 18): Fr1, Fr2, Fr3, Fr4 and Fr5. The first three fractions include at least a major peak.

Collagenase Assays

The collagenase assays were run on these samples using recombinant human skin collagenase, type 1 (MMP1) using a fluorogenic peptide substrate (assay 1) and a collagen substrate (assay 2).

Assay 1

This assay is described in Knight et al. (1992) FEBS Let. 296, 263–266. The method utilizes a fluorogenic peptide substrate (Mca-pro-leu-glu-leu-Dpa-ala-arg-$NH_2$) mimicking the active site of metalloproteinases. This substrate has a fluorescent group (Mca) at one end and a fluorescence quenching group (Dpa) at the other. In the intact substrate, the quenching group effectively masks the fluorescence. Upon enzyme cleavage of the substrate the fluorescence in the test tube increases.

Collagenase activation is described in Weingarten et al. (1985) Biochemistry 24, 6730. 1 μg was diluted to 100 μl with 50 mM Tris-HCl, 10 mM $CaCl_2$. pH 7.5, 1 μl at 10 mg/ml solution of trypsin (in 1 mM HCl) was added and incubated for 15 min at 20° C. Activation was terminated by adding 10 μl of Soybean trypsin inhibitor (SBTI, 5 mg/ml). To each microcuvette was added:

25 or 50 μl inhibitor (made up to 50 μl with H$_2$);

40 μl 50 mM Tris-HCl, 200 mM NaCl, 10 mM CaCl$_2$, pH 7.5;

8 μl activated collagenase (67 ng final); and

2 μl substrate (1 mM stock solution in DMSO, 20 μM final).

Fluorescence was recorded at $\lambda_{ex}$=328 nm, $\lambda_{em}$=393 nm.

Figure 19:
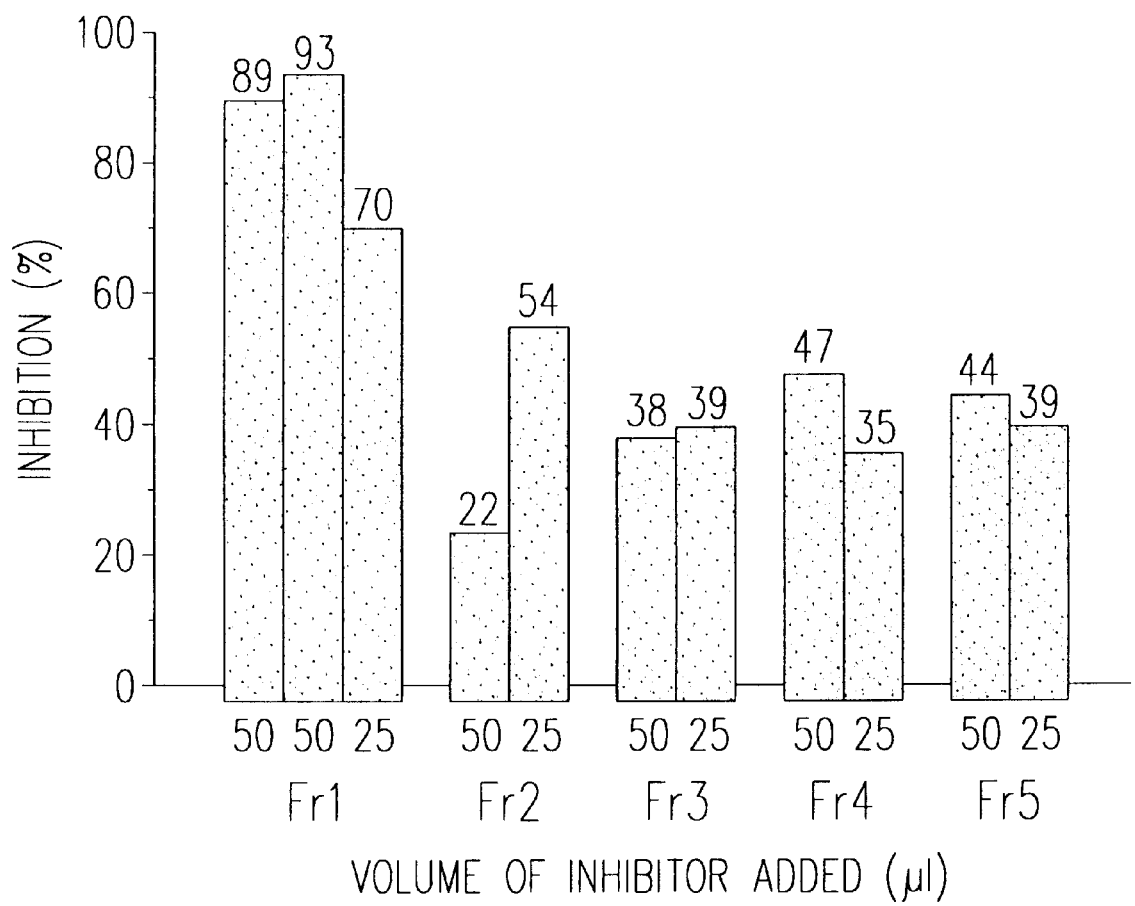
FIG. 19 shows the anti-collagenolytic effect of each sub-fraction shown in FIG. 18 at different tested volumes. collagenolytic inhibition of <10—10X FPLC fractions.

The results show that Fr1 is the most active fraction to inhibit the collagenase (FIG. 19). A lower level of activity is present in all other fractions. When tested on tadpole vertebrate collagenase, the enzyme was significantly inhibited by the shark cartilage extract (EC50 of about 10–20 μg/mL).

Assay 2

This assay is described in Welgus et al. (1979) JBC 256, 9511–9516. The method uses SDS-PAGE to examine cleavage by collagenase, type 1 (MMP1). Collagenase type 1 makes a single cut in the native collagen molecule giving two fragments of 75% and 25% the size of the original collagen. After cleavage for several hours, the reaction is monitored by separating the products from the substrate by SDS-PAGE. The ratio of cleaved to uncleaved collagen is assessed visually after staining the gels with Comassie blue (or silver stain).

21 ng of activated collagenase (see Assay 1) was added to 5 μg of calf skin collagen (Worthington) ± inhibitor in a final volume of 20 μl. Reactions were incubated for 16 h at 35° C., then stopped by adding SDS-PAGE sample with 40 mM EDTA, boiled and loaded on a 8% gel.

Results are summarized in the following table.

| SAMPLE | COLLAGEN STAINING | COLLAGEN FRAGMENT STAINING |
| --- | --- | --- |
| Collagen only (C) | ++++ | – |
| C + Enz | + | +++ |
| C + Enz + EDTA | ++++ | – |
| C + Enz + DUP | + | ++ |
| C + Enz + Fr1 | ++++ | – |
| C + Enz + Fr2 | +++ | + |
| C + Enz + Fr3 | +++ | + |
| C + Enz + Fr4 | +++ | + |
| C + Enz + Fr5 | +++ | + |
| C + Enz + >10 KDa | + | +++ |

EDTA 40 mM inhibited collagenase. The total liquid extract DUP showed a low anti-collagenolytic activity. Fractions 1 to 5 were active; the best active was fraction 1. The fraction of a molecular weight higher than 10 KDa showed no significant inhibitory activity.

COSMETIC APPLICATIONS AND COMPOSITIONS

The above tests and trials have shown that the cartilage extract of this invention may find numerous medical applications. Among the diverse activities recovered in this extract, anti-collagenolytic, anti-inflammatory and inhibitory effect on PKC-induced differentiation are particularly desirable in cosmetic applications. Since the cartilage extract of the present invention has shown an antagonist effect of PKC-mediated cellular events, and since such antagonist effect is suggested in the art as one improving the skin barrier repair function, a method for improving the barrier repair function in mammalian skin which comprises the step of applying to the skin a composition which comprises the cartilage extract and a pharmaceutically acceptable carrier, and such a composition are under the scope of this invention. Other or similar compositions can also be conceived to be used in a method for soothing skin or for reducing inflammation in mammalian skin. Inflammation can be caused by various agents such as chemical irritant, physical abrasion and exposure to ultraviolet radiation. Compositions and methods for inhibiting collagenase in skin are also contemplated. Collagenase and inflammation are linked to premature aging (degradation of collagen), and therefore the antagonist activities recovered in the cartilage extract could also be put to contribution in compositions and methods for retarding premature aging, and for regulating wrinkles or atrophy in mammalian skin. As causes of wrinkles or atrophy are listed, by way of examples, age, exposure to ultraviolet radiation or to environmental pollutant. Topical compositions may comprise an effective amount of shark cartilage, to be determined for each specific application. In general, these compositions may contain from about 0.1 to about 75 weight percent of a liquid 1× to 20× cartilage extract and from about 50 to 99.9 weight percent of a pharmaceutically acceptable vehicle. These compositions may contain an anti-oxidant such as an agent which prevents the formation of lipid peroxides in skin. Examples of such anti-oxidant are tocopherol, tocopherol derivatives, ascorbic acid, ascorbic acid derivatives and BHT. The compositions can be complemented with anti-inflammatory agents like a phospholipase A2 inhibitor or the botanically-derived anti-irritants cola and green tea extract. Topical compositions may take diverse forms such as solutions, suspensions, lotions, tinctures, gels, creams, sprays, emulsions, sticks, ointments or liposomes (at least a portion of the liquid cartilage extract being present in liposomes).

CONCLUSIONS

The process of the present invention has been demonstrated as one that provides for the production of cartilage extracts of a great clinical value. The shark cartilage extracts produced by this novel process comprises a multiplicity of activities that are recovered in good yields. The cartilage extracts, particularly the liquid extract and fractions thereof have a great potential since they are non-toxic to normal cells while they are effective in a large variety of diseases or conditions.

REQUIRED MATERIAL

Coolers

Surgical instruments

Meat chopper

Plastic bags

Industrial blender (Waring 3-speed blender bought from Fisher Scientific)

A system of purification of water (inverse osmosis and 0.1 μm filtration; Continental Water System, model PRE 2202, serial number 91089, Modulab Bioscience RQ/Polishing System bought from Fisher Scientific, Montreal, Quebec). This system provides an apyrogenic water of high quality.

A precision balance Mettler, series AE bought from Fisher Scientific

Centrifuge Sorvall RC-285 bought from DuPont Canada

Centrifuge CEPA

Nylon pocket of a porosity of 30 μM

An autoclave (automatic vapor sterilizer Sanyo, model MAC 350P)

Nalgene 500 mL containers sterilized at 132° C. for 10 minutes and dried for 35 minutes Conical filters of 24 μm porosity Whatman Reeve Angel Ultrafiltration column (Molecular weight cut-off: 500 KDa and 1 KD when applicable; Surface: 25 square feet; Flow: 130 L/minute; Inlet pressure: 30 psi; Outlet pressure: 5 psi; bought from Koch Membrane Systems Inc., Wilmington, Mass., USA)

Sanitary centrifuge pump (Monarch Industries, model ACE-S100, type A) for providing a 130 L/minute flow sterile hut (laminar flow hut NuAire bought from Ingram & Bell)

Millipack-60 0.22 µm sterile filters

Sterile clear or amber glass bottles

Concentrator DC-10 Amicon

Rotofor Biorad 170-2950

Amicon filters SIOY10, SIOY30 and SIOY100 of cut-off values of 10, 30 and 100 KD, respectively FPLC Pharmacia 216007 (computer Pharmacia 216014)

SEPHACRYL S-300™ (cross-linked co-polymer of allyl dextran and N,N methylene bisacrylamide) 26 mm/60 cm (Pharmacia)

Superose S-12 10 mm/30 cm (Pharmacia)

Lyophilizer Labconco 10273 A

This invention has been described hereinabove, and it should be appreciated that it would be well within the ability and the knowledge of the person skilled in the art, without departing from the teachings of this disclosure, to bring modifications by replacing some elements of this invention as practiced by their equivalents, which would achieve the same goal thereof. These obvious variations are deemed covered by this application.

What is claimed is:

1. A process for obtaining a liquid extract of cartilage having a substantial portion of the biologically active components present in intact cartilage, which comprises the following steps:
    a) homogenizing the cartilage in an aqueous solution in conditions which are non-denaturing towards biologically active components, until the cartilage is reduced to solid particles whose size is lower than or equal to about 500 µm;
    b) extracting said biologically active component into said aqueous solution which results in a mixture of solid particles and of a crude liquid extract having said biologically active components;
    c) separating said crude liquid extract from said solid particles; and
    d) further separating the crude liquid extract so as to obtain a final liquid extract containing cartilage molecules having a molecular weight lower than about 500 Kilodaltons (Kda);
with the proviso that the cartilage is not shark cartilage.

2. A process as defined in claim 1, wherein said conditions comprise a working temperature comprised between about 0 to 10° C.

3. A process as defined in claim 1, wherein said conditions comprise a working pH ranging from about 6 to about 8 for said aqueous solution.

4. A process as defined in claim 1, wherein said aqueous solution is purified water.

5. A process as defined in claim 1, wherein said cartilage and aqueous solution are in proportions of 1 Kilogram for about 1 liter or more aqueous solution volume.

6. A cartilage extract produced by the method of claim 1.

7. A process as defined in claim 1, wherein step b) is performed within 15 minutes to 24 hours.

8. A process as defined in claim 7, wherein step b) is performed within 15 minutes to 1 hour.

9. A topical formulation for treating diseases or disorders having one or more etiological components selected from the group consisting of tumor proliferation, angiogenesis, inflammation and collagenolysis, the topical formulation comprising a pharmaceutical composition comprising an effective amount of a shark cartilage extract and an antioxidant, said shark cartilage extract being prepared according to a process comprising the steps of:
    a) homogenizing the cartilage in an aqueous solution in conditions which are non-denaturing towards biologically active components, until the cartilage is reduced to solid particles whose size is lower than or equal to about 500µ;
    b) extracting said biologically active components into said aqueous solution which results in a mixture of solid particles and of a crude liquid extract having said biologically active components;
    c) separating said crude liquid extract from said solid particles; and
    d) further separating the crude liquid extract so as to obtain a final liquid extract containing cartilage molecules having a molecular weight lower than about 500 Kilodaltons (Kda).

10. A formulation as defined in claim 9, wherein the antioxidant is selected from the group consisting of tocopherol, tocopherol derivatives, ascorbic acid, ascorbic acid derivatives and butylated hydroxy-toluene.

11. A formulation as defined in claim 9, wherein the formulation is selected from the group consisting of solution, suspension, lotion, tincture, gel, cream, spray, emulsion, stick and ointment.

12. A formulation as defined in claim 9, wherein said formulation comprises liposomes comprising the cartilage extract.

13. A method for soothing mammalian skin which comprises the step of applying to the skin a composition as defined in claim 9.

14. A method for inhibiting collagenase activity in mammalian skin which comprises the step of applying to the skin a composition as defined in claim 9.

15. A method for reducing acne in mammalian skin which comprises the step of applying to the skin a formulation as defined in claim 9.

16. A method for reducing psoriasis in mammalian skin which comprises the step of applying to the skin a formulation as defined in claim 9.

17. A method for treating diseases or disorders having one or more etiological components selected from the group consisting of tumor proliferation, angiogenesis, inflammation and collagenolysis, the method comprising the step of administering to a patient in need of such treatment a formulation as defined in claim 9.

18. A method as defined in claim 17, wherein said diseases or disorders are selected from the group consisting of cancer, psoriasis, skin irritation and skin inflammation, arthritis and acne.

19. A formulation as defined in claim 9 additionally comprising an anti-inflammatory agent.

20. A formulation as defined in claim 19, wherein the anti-inflammatory agent is a phospholipase A2 inhibitor.

21. A formulation as defined in claim 19, wherein the anti-inflammatory agent is a botanically-derived anti-irritant.

22. A formulation as defined in claim 21, wherein the anti-inflammatory agent is selected from the group consisting of cola and green tea extract.

23. A method for reducing inflammation in mammalian skin which comprises the step of applying to the skin a formulation as defined in claim 9.

24. A method as defined in claim 23 wherein said inflammation is caused by physical abrasion.

25. A method as defined in claim 23 wherein said inflammation is caused by chemical irritant.

26. A method as defined in claim 23 wherein said inflammation is caused by exposure to ultraviolet radiation.

27. A method for treating diseases or disorders having one or more etiological components selected from the group consisting of inflammation and collagenolysis, the method comprising the step of administering to a patient in need of such treatment an effective amount of a shark cartilage extract, said shark cartilage extract being prepared according to a process which comprises the following steps:
   a) homogenizing the cartilage in an aqueous solution in conditions which are non-denaturing towards biologically active components, until the cartilage is reduced to solid particles whose size is lower than or equal to about 500 $\mu$.
   b) extracting said biologically active components into said aqueous solution which results in a mixture of solid particles and of a crude liquid extract having said biologically active components;
   c) separating said crude liquid extract from said solid particles; and
   d) further separating the crude liquid extract so as to obtain a final liquid extract containing cartilage molecules having a molecular weight lower than about 500 Kilodaltons (Kda).

28. A method as defined in claim 27, wherein said diseases or disorders are selected from the group consisting of cancer, psoriasis, arthritis, acne, skin irritation and skin inflammation.

\* \* \* \* \*